United States Patent
Jagtap et al.

(10) Patent No.: US 7,732,424 B2
(45) Date of Patent: Jun. 8, 2010

(54) PURINE DERIVATIVES AND METHODS OF USE THEREOF

(75) Inventors: Prakash Jagtap, North Andover, MA (US); Andrew L. Salzman, Belmont, MA (US)

(73) Assignee: Inotek Pharmaceuticals Corporation, Beverly, MA (US)

( * ) Notice: Subject to any disclaimer, the term of this patent is extended or adjusted under 35 U.S.C. 154(b) by 179 days.

(21) Appl. No.: 11/606,577

(22) Filed: Nov. 30, 2006

(65) Prior Publication Data

US 2007/0191301 A1  Aug. 16, 2007

Related U.S. Application Data

(60) Provisional application No. 60/740,795, filed on Nov. 30, 2005.

(51) Int. Cl.
*A61K 31/70* (2006.01)
*C07H 19/167* (2006.01)

(52) U.S. Cl. ........... 514/46; 536/27.62; 536/27.63

(58) Field of Classification Search ............ None
See application file for complete search history.

(56) References Cited

U.S. PATENT DOCUMENTS

| | | | |
|---|---|---|---|
| 3,819,613 A | 6/1974 | Kawazoe et al. |
| 3,832,341 A | 8/1974 | Duschinsky |
| 4,242,505 A | 12/1980 | Kawahara et al. |
| 4,443,836 A | 4/1984 | Horiuchi et al. |
| 4,968,697 A | 11/1990 | Hutchison |
| 5,140,015 A | 8/1992 | Olsson et al. |
| 5,206,222 A | 4/1993 | Forman et al. |
| 5,219,840 A | 6/1993 | Gadient et al. |
| 5,278,150 A | 1/1994 | Olsson et al. |
| 5,280,015 A | 1/1994 | Jacobson et al. |
| 5,407,793 A | 4/1995 | Del Nido et al. |
| 5,443,836 A | 8/1995 | Downey et al. |
| 5,589,467 A | 12/1996 | Lau et al. |
| 5,604,210 A | 2/1997 | Nagaoka et al. |
| 5,789,416 A | 8/1998 | Lum et al. |
| 6,180,615 B1 | 1/2001 | Zablocki et al. |
| 6,214,807 B1 | 4/2001 | Zablocki et al. |
| 6,326,359 B1 | 12/2001 | Monaghan et al. |

(Continued)

FOREIGN PATENT DOCUMENTS

DE  2342479 A1  3/1975

(Continued)

OTHER PUBLICATIONS

International Search Report and Written Opinion issued for International Patent Application No. PCT/US2006/045845.

(Continued)

*Primary Examiner*—Lawrence E Crane
(74) *Attorney, Agent, or Firm*—Lahive & Cockfield, LLP; Jane E. Remillard; Brian C. Trinque

(57) ABSTRACT

The present invention relates to Purine Derivatives; compositions comprising an effective amount of a Purine Derivative; and methods for reducing an animal's core body temperature, protecting an animal's heart against myocardial damage during cardioplegia; or for treating or preventing a cardiovascular disease, a neurological disorder, an ophthalmic condition, an ischemic condition, a reperfusion injury, obesity, a wasting disease, or diabetes, comprising administering an effective amount of a Purine Derivative to an animal in need thereof. The Purine Derivatives include compounds of the following formula:

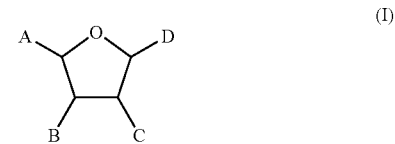

(I)

Figure 1:
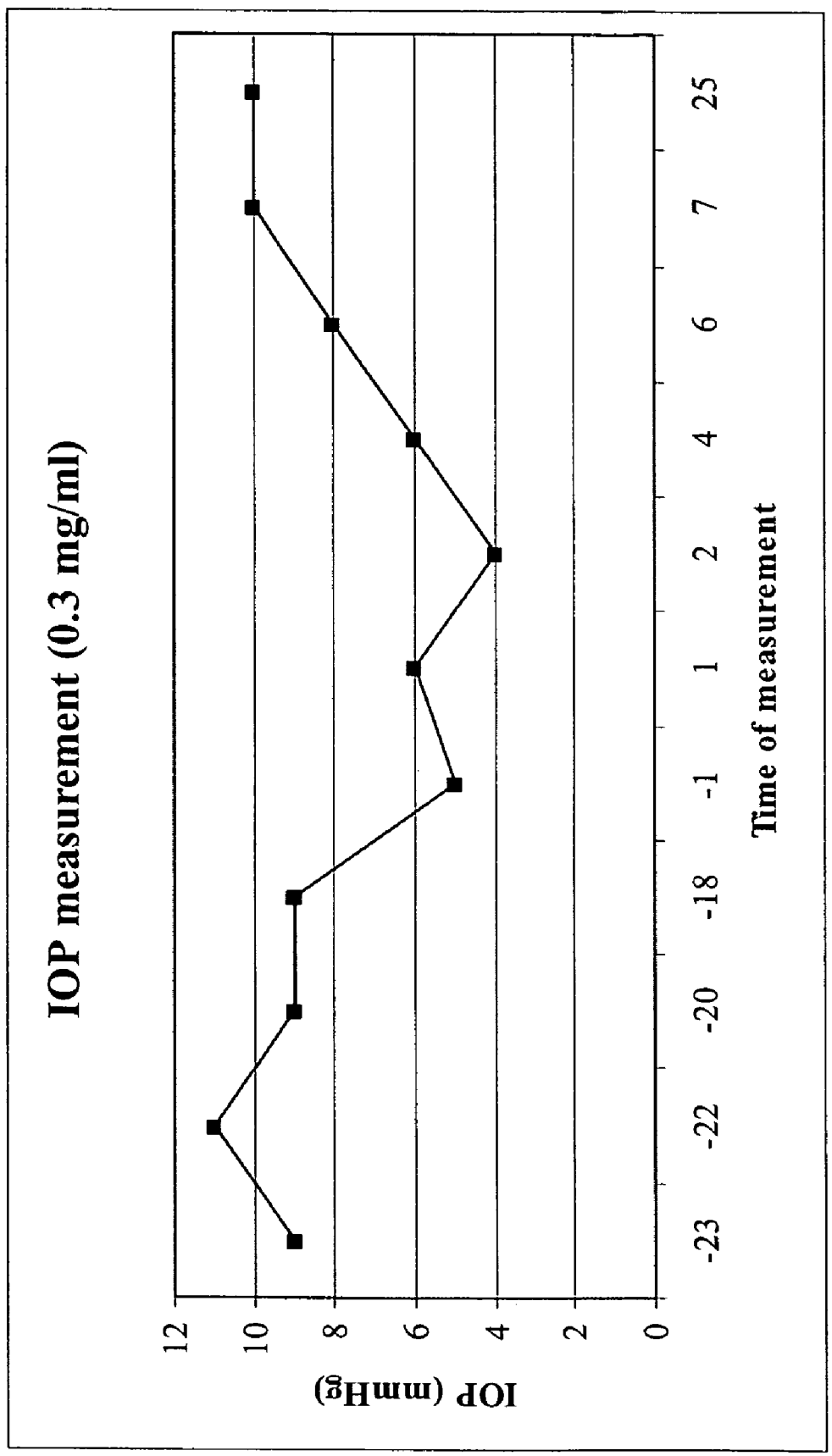

or a pharmaceutically acceptable salt thereof
wherein
A is —$CH_2OH$
B and C are —OH:
D is

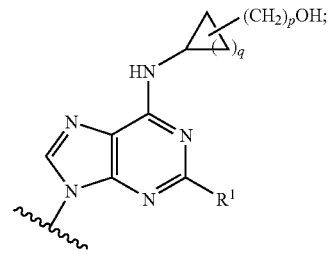

A and B are trans with respect to each other:
B and C are cis with respect to each other:
C and D are cis or trans with respect to each other:
$R^1$ is —H, -halo, —CN, —$N(R^2)_2$, —$OR^2$, —$SR^2$, —NHC(O)$R^2$, —NHC(O)N($R^2$)$_2$, —NHC(O)O$R^2$, —C(O)O$R^2$, —C(O)$R^2$, —C(O)N($R^2$)$_2$, —OC(O)N($R^2$)$_2$, —C(halo)$_3$, or —$NO_2$;
each $R^2$ is independently —H, —$C_1$-$C_{10}$ alkyl, —$C_2$-$C_6$ alkenyl, —$C_2$-$C_6$ alkynyl, —$(CH_2)_n$-aryl, —$(CH_2)_n$-(3- to 7-membered monocyclic heterocycle), —$(CH_2)_n$-(8- to 12-membered bicyclic heterocycle), —$(CH_2)_n$—($C_3$-$C_8$ monocyclic cycloalkyl), —$(CH_2)_n$—($C_3$-$C_8$ monocyclic cycloalkenyl), —$(CH_2)_n$—($C_8$-$C_{12}$ bicyclic cycloalkyl), or —$(CH_2)_n$—($C_8$-$C_{12}$ bicyclic cycloalkenyl);
each n is an integer ranging from 0 to 6;
each p is an integer ranging from 1 to 6; and
each q is an integer ranging from 1 to 6.

35 Claims, 5 Drawing Sheets

U.S. PATENT DOCUMENTS

| | | |
|---|---|---|
| 6,358,536 B1 | 3/2002 | Thomas |
| 6,368,573 B1 | 4/2002 | Leung |
| 6,403,567 B1 | 6/2002 | Zablocki et al. |
| 6,426,337 B1 | 7/2002 | Cox et al. |
| 6,440,948 B1 | 8/2002 | Zablocki et al. |
| 6,448,236 B1 | 9/2002 | Monaghan et al. |
| 6,525,032 B2 | 2/2003 | Mantell et al. |
| 6,528,494 B2 | 3/2003 | Cox et al. |
| 6,531,457 B2 | 3/2003 | Linden et al. |
| 6,534,486 B1 | 3/2003 | Allen et al. |
| 6,544,960 B1 | 4/2003 | Eldred et al. |
| 6,605,597 B1 | 8/2003 | Zablocki et al. |
| 6,638,914 B1 | 10/2003 | Fishman et al. |
| 6,753,322 B2 | 6/2004 | Mantell et al. |
| 6,875,751 B2 | 4/2005 | Imbach et al. |
| 6,921,753 B2 | 7/2005 | Mantell et al. |
| 7,238,676 B2 | 7/2007 | Mantell et al. |
| 7,423,144 B2 | 9/2008 | Jagtap et al. |
| 2001/0051612 A1 | 12/2001 | Cristalli |
| 2002/0082240 A1 | 6/2002 | Linden et al. |
| 2003/0013675 A1 | 1/2003 | Yeadon et al. |
| 2003/0055021 A1 | 3/2003 | DeNinno et al. |
| 2003/0078212 A1 | 4/2003 | Li et al. |
| 2004/0063658 A1 | 4/2004 | Roberts et al. |
| 2005/0020532 A1 | 1/2005 | Elzein et al. |
| 2005/0282768 A1 | 12/2005 | Jagtap et al. |
| 2006/0034941 A1 | 2/2006 | Dobson |
| 2006/0128652 A1 | 6/2006 | Jagtap et al. |
| 2007/0191301 A1 | 8/2007 | Jagtap et al. |
| 2007/0238694 A1 | 10/2007 | Salzman et al. |

FOREIGN PATENT DOCUMENTS

| | | |
|---|---|---|
| EP | 0322242 B1 | 6/1989 |
| FR | 2186470 | 1/1974 |
| WO | WO-94/02497 A1 | 2/1994 |
| WO | WO-95/02604 A1 | 1/1995 |
| WO | WO 95/11681 A1 | 5/1995 |
| WO | WO-96/02553 A2 | 2/1996 |
| WO | WO-97/33590 A1 | 9/1997 |
| WO | WO-97/33879 A1 | 9/1997 |
| WO | WO-98/08855 A2 | 3/1998 |
| WO | WO-98/50047 A1 | 11/1998 |
| WO | WO-99/20284 A1 | 4/1999 |
| WO | WO-01/19360 A2 | 3/2001 |
| WO | WO-01/40245 A1 | 6/2001 |
| WO | WO-01/45715 A2 | 6/2001 |
| WO | WO-02/055085 A2 | 7/2002 |
| WO | WO-02/083152 A1 | 10/2002 |
| WO | WO-03/029264 A2 | 4/2003 |

OTHER PUBLICATIONS

Al-Mughales, J. et al., "The chemoattractant activity of rheumatoid synovial fluid for human lymphocytes is due to multiple cytokines," *Clin. Exp. Immunol.*, vol. 106:230-236 (1996).

Baraldi, Pier Giovanni et al., "Synthesis and Biological Activity of a New Series of $N^6$-Arylcarbamoyl, 2-(Ar)alkynyl-$N^6$-arylcarbamoyl, and $N^6$-Carboxamido Derivatives of Adenosine-5'-$N$-ethyluronamide as $A_1$ and $A_3$ Adenosine Receptor Agonists," *J. Med. Chem.*, vol. 41:3174-3185 (1998).

Beukers, Margot W. et al., "$N^6$-Cyclopentyl-2-(3-phenylaminocarbonyltriazene-1-yl)adenosine (TCPA), a Very Selective Agonist with High Affinity for the Human Adenosine $A_1$ Receptor," *J. Med. Chem.*, vol. 46:1492-1503 (2003).

Beukers, Margot W. et al., "New, Non-Adenosine, High-Potency Agonists for the Human Adenosine A2B Receptor with an Improved Selectivity Profile Compared to the Reference Agonists $N$-Ethylcarboxamidoadenosine," *Journal of Medicinal Chemistry*, vol. 47(15):3707-3709 (2004).

Bouma, Maarten G. et al., "Differential Regulatory Effects of Adenosine on Cytokine Release by Activated Human Monocytes," *The Journal of Immunology*, vol. 153:4159-4168 (1994).

Bradley, Karri K. et al., "Purine Nucleoside-Dependent Inhibition of Cellular Proliferation in 1321N1 Human Astrocytoma Cells," *The Journal of Pharmacology and Experimental Therapeutics*, vol. 299(2):748-752 (2001).

Broadley, Kenneth J. et al., "Drugs modulating adenosine receptors as potential therapeutic agents for cadiovascular diseases," *Exp. Opin. Ther. Patents*, vol. 10(11):1669-1692 (2000).

Bruns, Robert F., "Adenosine receptor activation in human fibroblasts: nucleoside agonists and antagonists," *Can. J. Physiol. Pharmacol.*, vol. 58:673-691 (1980).

Bruns, Robert F. et al., "Characterization of the $A_2$ Adenosine Receptor Labeled by [$^3$H]NECA in Rat Striatal Membrans," *Biological Pharmacology*, vol. 89:331-346 (1986).

Camaioni, Emidio et al., "Adenosine Receptor Agonists: Synthesis and Biological Evaluation of the Diastereoisomers of 2-(3-Hydroxy-3-phenyl-1-propyn-1-yl)NECA," *Bioorganic & Medicinal Chemistry*, vol. 5(12):2267-2275 (1997).

Cristalli, Gloria et al., "2-Alkynyl Derivatives of Adenosine-5'-$N$-ethyluronamide: Selective $A_2$ Adenosine Receptor Agonists with Potent Inhibitory Activity on Platelet Aggregation," *J. Med. Chem.*, vol. 37:1720-1726 (1994).

Cristalli, Gloria et al., "2-Alkynyl Derivatives of Adenosine and Adenosine-5'-$N$-ethyluronamide as Selective Agonists at $A_2$ Adenosine Receptors," *J. Med. Chem.*, vol. 35:2363-2368 (1992).

Cristalli, Gloria et al., "2-Aralkynyl and 2-Heteroalkynyl Derivatives of Adenosine-5'-$N$-ethyluronamide as Selective $A_{2a}$ Adenosine Receptor Agonists," *J. Med. Chem.*, vol. 38:1462-1472 (1995).

Dalpiaz, Alessandro et al., "Synthesis and Study of 5'-Ester Prodrugs of $N^6$-Cyclopentyladenosine, a Selective $A_1$ Receptor Agonist," *Pharmaceutical Research*, vol. 18(4):531-536 (2001).

De Lean, Andre et al., "Validation and Statistical Analysis of a Computer Modeling Method for Quantitative Analysis of Radioligand Binding Data for Mixtures of Pharmacological Receptor Subtypes," *Molecular Pharmacology*, vol. 21:5-16 (1982).

DeNinno, Michael P. et al., "3'-Aminoadenosine-5'-uronamides: Discovery of the First Highly Selective Agonist at the Human Adenosine $A_3$ Receptor," *J. Med. Chem.*, vol. 46:353-355 (2003).

Fisher, Charles J. Jr. et al., "Treatment of Septic Shock with the Tumor Necrosis Factor Receptor : Fc Fusion Protein," *N. Engl. J. Med.*, vol. 334(26):1697-1702 (1996).

Follmann, Hartmut et al., "Adenine Nucleosides in Solution: Circular Dichroism Studies and Base Conformation," *Eur. J. Biochem.*, vol. 58:31-41 (1975).

Francis, John E. et al., "Highly Selective Adenosine A2 Receptor Agonists in a Series of N-Alkylated 2-Aminoadenosines," *J. Med. Chem.*, vol. 34:2570-2579 (1991).

Haskó, György et al., "Adenosine Receptor Agonists Differentially Regulate IL-10, TNF-α, and Nitric Oxide Production in RAW 264.7 Macrophages and in Endotoxemic Mice," *The Journal of Immunology*, vol. 157:4634-4640 (1996).

Homma, Hiroshi et al., "Nucleosides and Nucleotides. 112. 2-(1Hexyn-1-yl)adenosine-5'-uronamides: A New Entry of Selective $A_2$ Adenosine Receptor Agonists with Potent Antihypertensive Activity," *J. Med. Chem.*, vol. 35:2881-2890 (1992).

Hutchison, Alan J. et al., "2-(Arylalkylamino)adenosin-5'-uronamides: A New Class of Highly Selective Adenosine $A_2$ Receptor Ligands," *J. Med. Chem.*, vol. 33:1919-1924 (1990).

Jagtap, Prakash G. et al., "2-($N$-Acyl) and 2-$N$-acyl-$N^6$-substituted analogues of adenosine and their affinity at the human adenosine receptors," *Bioorganic & Medicinal Chemistry Letters*, vol. 14:1495-1498 (2004).

Klotz, K.-N. et al., "Comparative pharmacology of human adenosine receptor subtypes—characterization of stably transfected receptors in CHO cells," *Naunyn-Schmiedeberg's Arch. Pharmacol.*, vol. 357:1-9 (1998).

Klotz, Karl-Norbert et al., "Photoaffinity Labeling of $A_1$-adenosine Receptors," *The Journal of Biological Chemistry*, vol. 260(27):14659-14664 (1985).

Knutsen, Lars J.S. et al., "N-Substituted Adenosines as Novel Neuroprotective $A_1$ Agonists with Dimished Hypotensive Effects," *J. Med. Chem.*, vol. 42:3463-3477 (1999).

Kunkel, Steven L. et al., "The role of chemokines in inflammatory joint disease," *Journal of Leukocyte Biology*, vol. 59:6-12 (1996).

Lichtenthaler, F.W. et al., "Nucleosides, XVIII[1]. Improved Preparation of Nucleoside 5'-Nitrates," *Synthesis*, vol. 27:199-201 (1973).

Lohse, Martin J. et al., "8-Cyclopentyl-1,3-dipropylxanthine (DPCPX)—a selective high affinity antagonist radioligand for $A_1$ adenosine receptors," *Naunyn-Schmiedeberg's Arch. Pharmacol.*, vol. 336:204-210 (1987).

Mager, P.P. et al., "Molecular simulation applied to 2-($N'$-alkylidenehydrazino)- and 2-($N''$-aralkylidenehydrazino)adenosine $A_2$ agonists," *Eur. J. Med. Chem.*, vol. 30:15-25 (1995).

Matsuda, Akira et al., "Nucleosides and Nucleotides. 103. 2-Alkynyladenosines: A Novel Class of Selective Adenosine $A_2$ Receptor Agonists with Potent Antihypertensive Effects," *J. Med. Chem.*, vol. 35:241-252 (1992).

McKenzie, Sheila G. et al., "Effects of Adenosine and Related Compounds on Adenylate Cyclase and Cyclic AMP Levels in Smooth Muscle," *European Journal of Pharmacology*, vol. 41:193-203 (1977).

McWhinney, Charlene D. et al., "Activation of adenosine $A_3$ receptors on macrophages inhibits tumor necrosis factor-α," *European Journal of Pharmacology*, vol. 310:209-216 (1996).

Missiaen, Ludwig et al., "Effect of adenine nucleosides on myo-inositol-1,4,5-trisphosphate-induced calcium release," *Biochem. J.*, vol. 325:661-666 (1997).

Moos, Walter H. et al., "$N^6$-Cycloalkyladenosines. Potent $A_1$-Selective Adenosine Agonists," *Journal of Medicinal Chemistry*, vol. 28(10):1383-1384 (1985).

Müller, C.E. et al., "Adenosine Receptor Ligands-Recent Developments Part I. Agonists," *Current Medicinal Chemistry*, vol. 7:1269-1288 (2000).

Nair, Vasu et al., "Novel, Stable Congeners of the Antiretroviral Compound 2', 3'-Dideoxyadenosine," *J. Am. Chem. Soc.*, vol. 111:8502-8504 (1989).

Niiya, Kazunori et al., "2-($N'$-Alkylidenehydrazino)adenosines: Potent and Selective Coronary Vasodilators," *J. Med. Chem.*, vol. 35:4557-4561 (1992).

Ohno, Michihiro et al., "Modulation of adenosine receptor affinity and intrinsic efficacy in adenine nucleosides substituted at the 2-position," *Bioorganic & Medicinal Chemistry*, vol. 12:2995-3007 (2004).

Ongini, Ennio et al., "Pharmacology of adenosine $A_{2A}$ receptors," *TiPS*, vol. 17:364-372 (1996).

Parmely, Michael J. et al., "Adenosine and a Related Carbocyclic Nucleoside Analogue Selectively Inhibit Tumor Necrosis Factor-α Production and Protect Mice against Endotoxin Challenge," *The Journal of Immunology*, vol. 151(1):389-396 (1993).

Pitcher, Graham M. et al., "Paw withdrawal threshold in the von Frey hair test is influenced by the surface on which the rat stands," *Journal of Neuroscience Methods*, vol. 87:185-193 (1999).

Reinhart, Konrad et al., "Assessment of the safety and efficacy of the monoclonal anti-tumor necrosis factor antibody-fragment, MAK 195F, in patients with sepsis and septic shock: A multicenter, randomized, placebo-controlled, dose-ranging study," *Crit. Care Med.*, vol. 24(5):733-742 (1996).

Reinstein, Leon J. et al., "Suppression of Lipopolysaccharide-stimulated Release of Tumor Necrosis Factor by Adenosine: Evidence for $A_2$ Receptors on Rat Kupffer Cells," *Hepatology*, vol. 19:1445-1452 (1994).

Riché, Florence et al., "High tumor necrosis factor serum level is associated with increased survival in patients with abdominal septic shock: A prospective study in 59 patients," *Surgery*, vol. 120(5):801-807 (1996).

Rieger, Jayson M. et al., "Design, Synthesis, and Evaluation of Novel $A_{2A}$ Adenosine Receptor Agonists," *J. Med. Chem.*, vol. 44:531-539 (2001).

Roelen, Harlof et al., "$N^6$, C8-Disubstituted Adeonsine Derivatives as Partial Agonists for Adenosine $A_1$ Receptors," *J. Med. Chem.*, vol. 39:1463-1471 (1996).

Sajjadi, Fereydoun G. et al., "Inhibition of TNF-α Expression by Adenosine," *The Journal of Immunology*, vol. 156:3435-3442 (1996).

Schleef, Raymond R. et al., "The Effect of Fibrin on Endothelial Cell Migration in Vitro," *Tissue & Cell*, vol. 14(4):629-636 (1982).

Shuman, Dennis A. et al., "The Synthesis of Nucleoside Sulfamates Related to Nucleocidin," *Journal of the American Chemical Society*, vol. 92(11):3434-3440 (1970).

Thompson, Robert D. et al., "Activity of N6-Substituted 2-Chloroadenosines at $A_1$ and $A_2$ Adeonsine Receptors," *J. Med. Chem.*, vol. 34:3388-3390 (1991).

van der Wenden, Eleonora M. et al., "5'Substituted Adenosine Analogs as New High-Affinity Partial Agonists for the Adenosine $A_1$ Receptor," *J. Med. Chem.*, vol. 41:102-108 (1998).

van Tilburg, Erica W. et al., "2,5'-Disubstituted Adenosine Derivatives: Evaluation of Selectivity and Efficacy for the Adenosine $A_1$, $A_{2A}$ and $A_3$ Receptor," *J. Med. Chem.*, vol. 45:420-429 (2002).

Virág, László et al., "Effects of poly(ADP-ribose) polymerase inhibition on inflammatory cell migration in a murine model of asthma," *Med. Sci. Monit.*, vol. 10(3):BR77-83 (2004).

Vittori, Sauro et al., "2-Alkenyl and 2-Alkyl Derivatives of Adenosine and Adenosine-5'-$N$-Ethyluronamide: Different Affinity and Selectivity of $E$- and $Z$-Diastereomers at $A_{2A}$ Adenosine Receptors," *J. Med. Chem.*, vol. 39:4211-4217 (1996).

Vittori, Sauro et al., "$N$- Cycloalkyl Derivatives of Adenosine and 1-Deazaadenosine as Agonists and Partial Agonists of the $A_1$ Adenosine Receptor," *J. Med. Chem.*, vol. 43:250-260 (2000).

Viziano, Monica et al., "2-[$N'$-(E-Arylallylidene)hydrazino]adenosines Showing $A_{2a}$ Adenosine Agonist Properties and Vasodilation Activity," *J. Med. Chem.*, vol. 38:3581-3585 (1995).

International Preliminary Report on Patentability for Application No. PCT/US2007/007146, dated Sep. 23, 2008.

International Search Report for Application No. PCT/US05/33476, dated Jan. 2, 2008.

European Office Action for Application No. 06838681.2, dated Nov. 13, 2008.

Supplementary European Search Report for Application No. 05757108, dated Jun. 4, 2007.

International Search Report for Application No. PCT/US07/07146, dated Oct. 10, 2007.

PURINE DERIVATIVES AND METHODS OF USE THEREOF

REFERENCE TO RELATED APPLICATIONS

This application claims the benefit of U.S. Provisional Application No. 60/740,795, filed Nov. 30, 2005, which is incorporated by reference herein in its entirety.

1. FIELD OF THE INVENTION

The present invention relates to Purine Derivatives; compositions comprising an effective amount of a Purine Derivative; and methods for reducing an animal's core body temperature, protecting an animal's heart against myocardial damage during cardioplegia; or for treating or preventing a cardiovascular disease, a neurological disorder, an ophthalmic condition, an ischemic condition, a reperfusion injury, obesity, a wasting disease, or diabetes, comprising administering an effective amount of a Purine Derivative to an animal in need thereof.

2. BACKGROUND OF THE INVENTION

Adenosine is a naturally occurring purine nucleoside that is ubiquitous in mammalian cell types. Adenosine exerts its biological effects by interacting with $A_1$, $A_2$ (further subclassified as $A_{2A}$ and $A_{2B}$) and $A_3$ cell surface receptors, which modulate important physiological processes.

The $A_1$ and $A_{2A}$ receptor subtypes are believed to play complementary roles in adenosine's regulation of a cell's energy supply. Adenosine, which is a metabolic product of ATP, diffuses from the cell and locally activates the $A_1$ receptor to decrease the oxygen demand or activates the $A_{2A}$ receptor to increase the oxygen supply, thereby reinstating the balance of energy supply and demand within the tissue. The combined action of $A_1$ and $A_2$ subtypes increases the amount of available oxygen to tissue and protects cells against damage caused by a short-term imbalance of oxygen. One of the important functions of endogenous adenosine is to prevent tissue damage during traumas such as hypoxia, an ischemic condition, hypotension and seizure activity.

In addition, modulation of $A_1$ receptors slows conduction velocity in the heart's atrioventricular node, resulting in the normalization of supraventricular tachycardias and control of cardiac ventricular rate during atrial fibrillation and flutter. Modulation of $A_{2A}$ receptors also regulates coronary vasodilation.

Adenosine is also a neuromodulator, which modulates molecular mechanisms underlying many aspects of physiological brain function by mediating central inhibitory effects. An increase in neurotransmitter release follows traumas such as hypoxia, ischemia and seizures. Neurotransmitters are ultimately responsible for neural degeneration and neural death, which can cause brain damage or death. Adenosine is thought to be an endogenous anticonvulsant agent that inhibits glutamate release from excitory neurons and neuronal firing. Adenosine agonists, therefore, are useful as antiepileptic agents.

Adenosine plays an important role as a cardioprotective agent. Levels of endogenous adenosine increase in response to ischemia and hypoxia and protect cardiac tissue during and after trauma (preconditioning). Adenosine agonists thus are useful as cardioprotective agents.

The preparation and use of a number of adenosine $A_1$ receptor agonists have been described (Moos et al., *J. Med. Chem.* 28:1383-1384 (1985); Thompson et al., *J. Med. Chem.* 34:3388-3390 (1991); Vittori et al., *J. Med. Chem.* 43:250-260 (2000); Roelen et al., *J. Med. Chem,* 39:1463-1471 (1996); van der Wenden et al., *J. Med. Chem.* 41102-108 (1998); Dalpiaz et al., *Pharm. Res.* 18:531-536 (2001); Beakers et al., *J. Med. Chem.* 46, 1492-1503 (2003); U.S. Pat. No. 5,589,467 to Lau et al.; U.S. Pat. No. 5,789,416, to Lum et al.; and C. E. Muller, *Current Medicinal Chemistry* 2000, 7, 1269-1288).

The citation of any reference in Section 2 of this application is not an admission that the reference is prior art to this application.

3.1 SUMMARY OF THE INVENTION

In one embodiment, the invention provides compounds having the Formula (I):

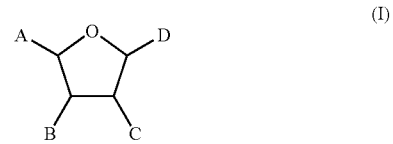

(I)

and pharmaceutically acceptable salts thereof, wherein
A is —$CH_2OH$;
B and C are —OH;
D is:

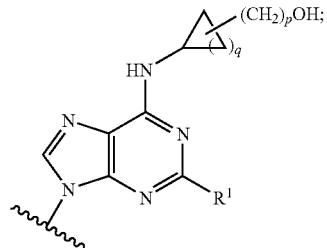

A and B are trans with respect to each other;
B and C are cis with respect to each other;
C and D are cis or trans with respect to each other;
$R^1$ is —H, -halo, —CN, —N($R^2$)$_2$, —O$R^2$, —S$R^2$, —NHC(O)$R^2$, —NHC(O)N($R^2$)$_2$, —NHC(O)O$R^2$, —C(O)O$R^2$, —C(O)$R^2$, —C(O)N($R^2$)$_2$, —OC(O)N($R^2$)$_2$, —C(halo)$_3$, or —$NO_2$;
each $R^2$ is independently —H, —$C_1$-$C_{10}$ alkyl, —$C_2$-$C_6$ alkenyl, —$C_2$-$C_6$ alkynyl, —(CH$_2$)$_n$-aryl, —(CH$_2$)$_n$-(3- to 7-membered monocyclic heterocycle), —(CH$_2$)$_n$-(8- to 12-membered bicyclic heterocycle), —(CH$_2$)$_n$—($C_3$-$C_8$ monocyclic cycloalkyl), —(CH$_2$)$_n$—($C_3$-$C_8$ monocyclic cycloalkenyl), —(CH$_2$)$_n$—($C_8$-$C_{12}$ bicyclic cycloalkyl), or —(CH$_2$)$_n$—($C_8$-$C_{12}$ bicyclic cycloalkenyl);
each n is an integer ranging from 0 to 6;
each p is an integer ranging from 1 to 6; and
each q is an integer ranging from 1 to 6.

A compound of Formula (I) or a pharmaceutically acceptable salt thereof (a "Purine Derivative") is useful for: (i) treating or preventing a cardiovascular disease, a neurological disorder, an ophthalmic condition, an ischemic condition, a reperfusion injury, obesity, a wasting disease, or diabetes (each being a "Condition"); (ii) reducing an animal's core body temperature; or (iii) protecting an animal's heart against myocardial damage during cardioplegia.

The invention also provides compositions comprising an effective amount of a Purine Derivative and a physiologically acceptable carrier or vehicle. The compositions are useful for: (i) treating or preventing a Condition; (ii) reducing an animal's core body temperature; or (iii) protecting an animal's heart against myocardial damage during cardioplegia.

The invention further provides methods for: (i) treating or preventing a Condition; (ii) reducing an animal's core body temperature; or (iii) protecting an animal's heart against myocardial damage during cardioplegia, comprising administering an effective amount of a Purine Derivative to an animal in need thereof.

3.2 BRIEF DESCRIPTION OF THE DRAWINGS

Figure 2:
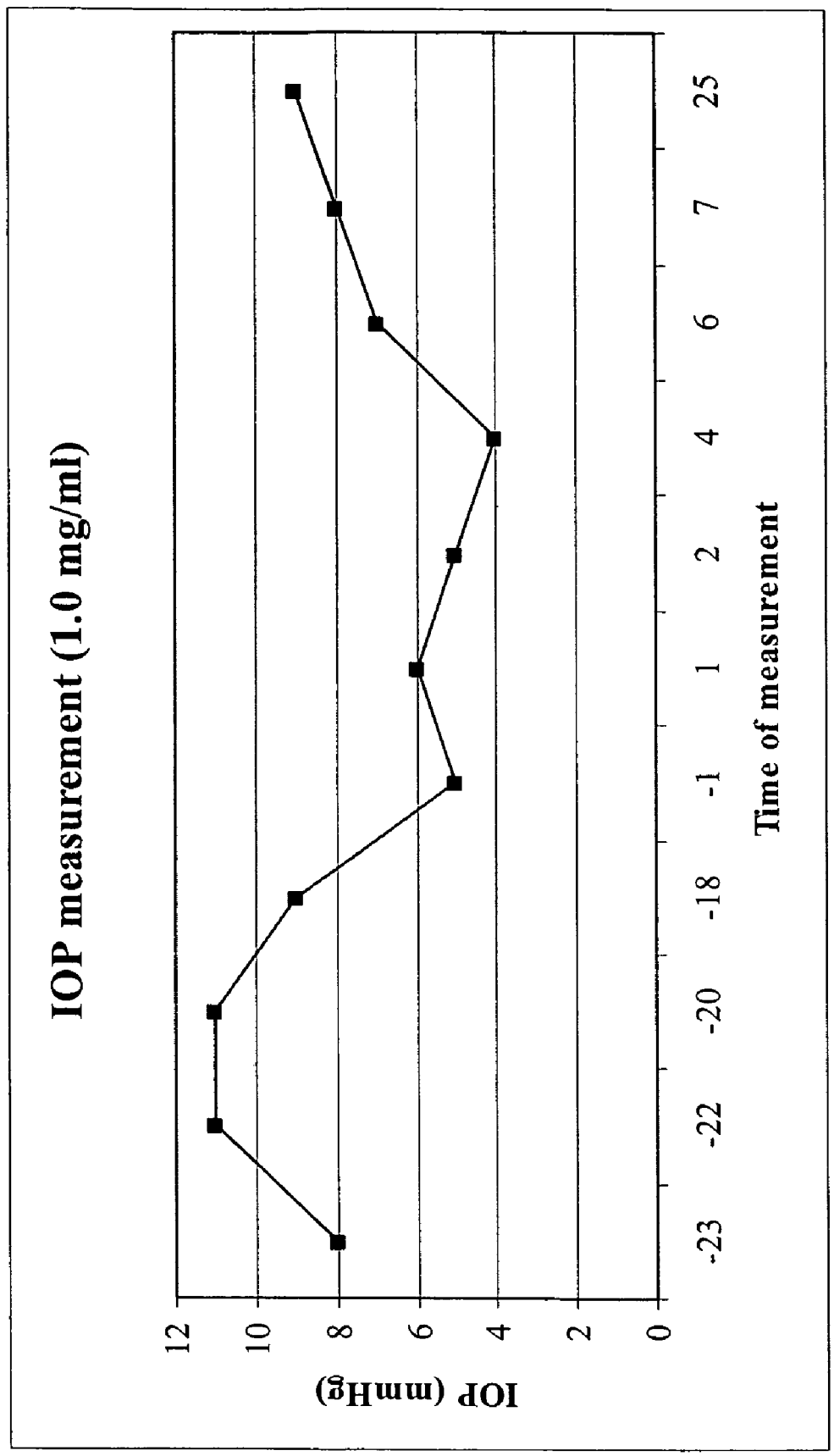
Figure 3:
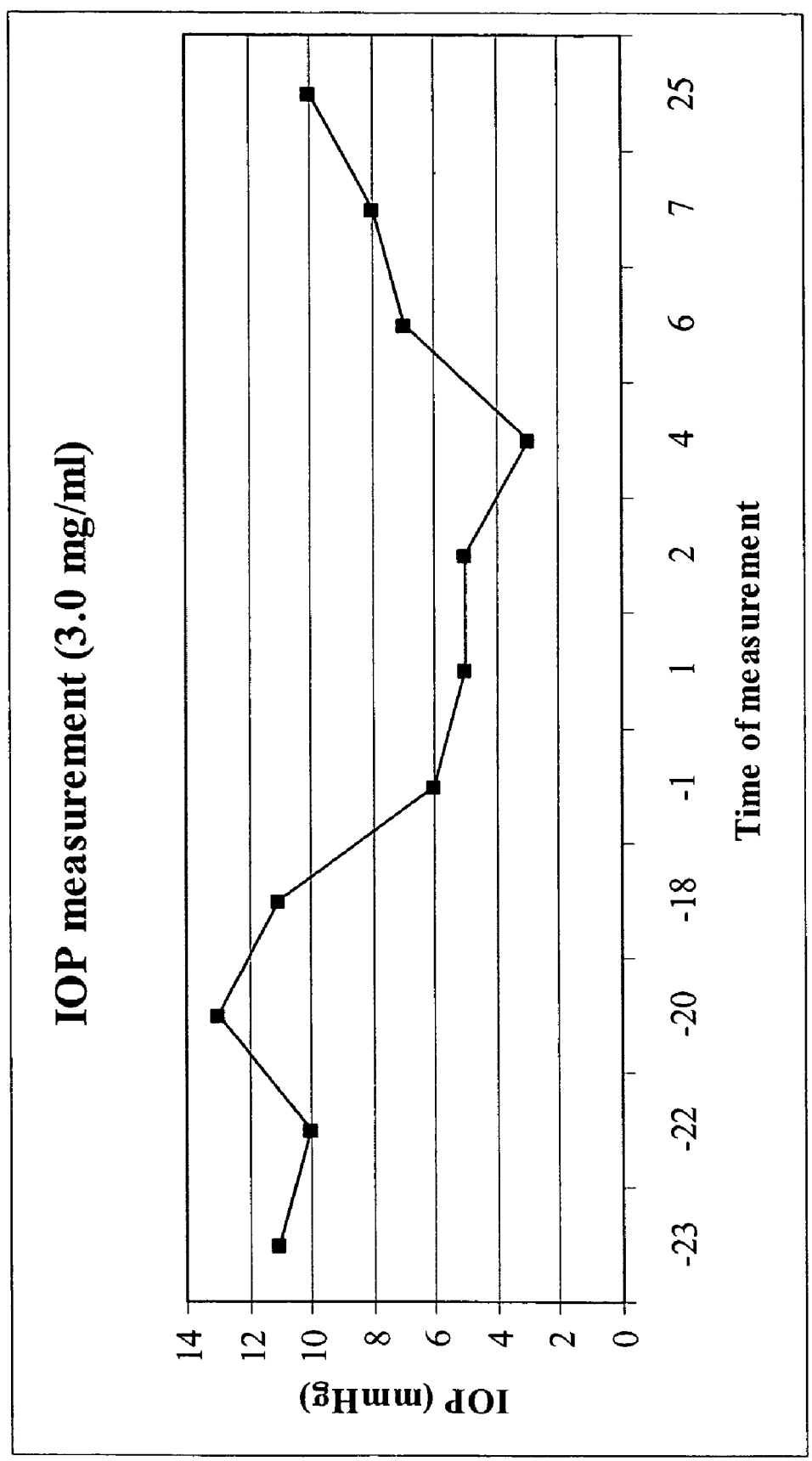
Figure 4:
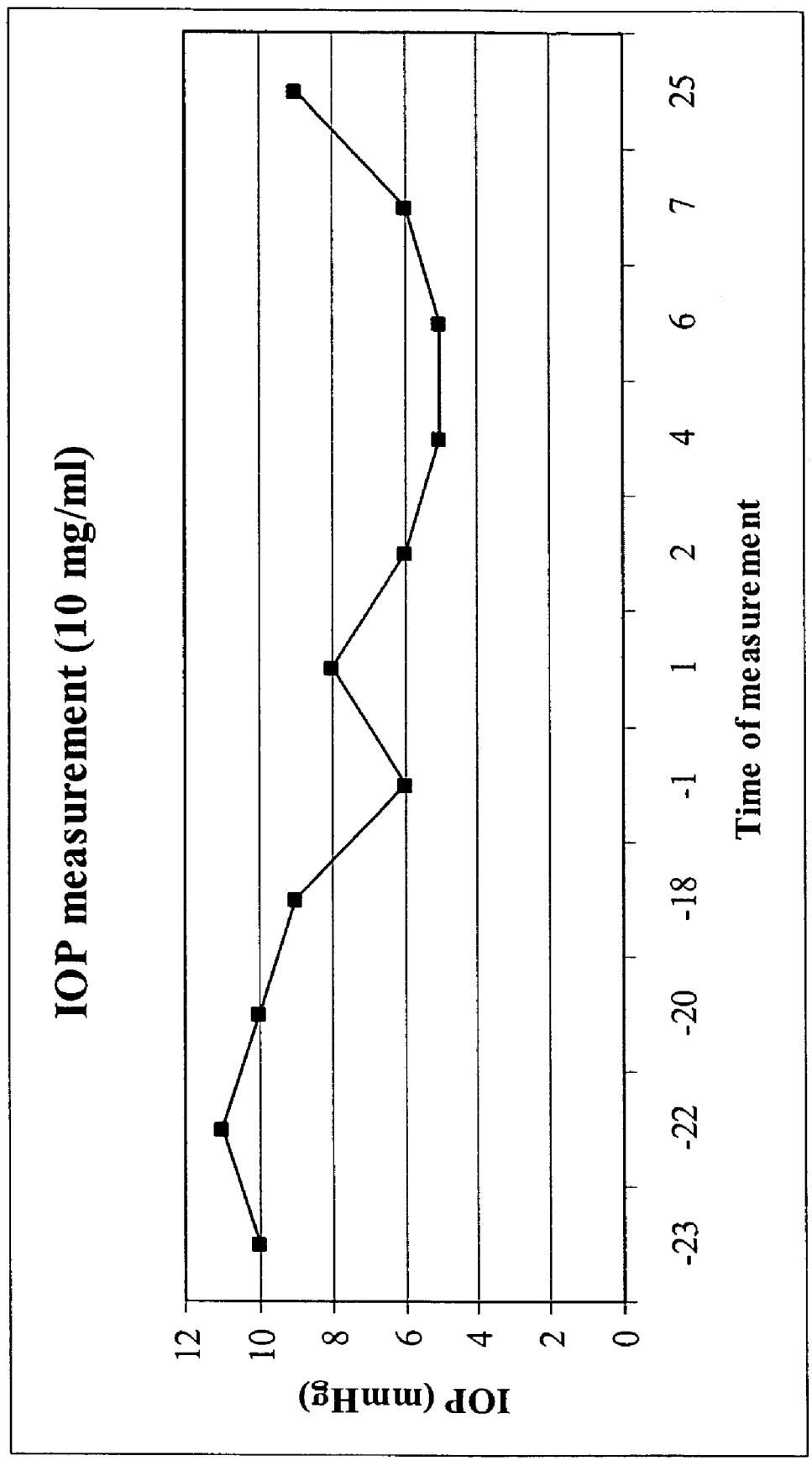
Figure 5:
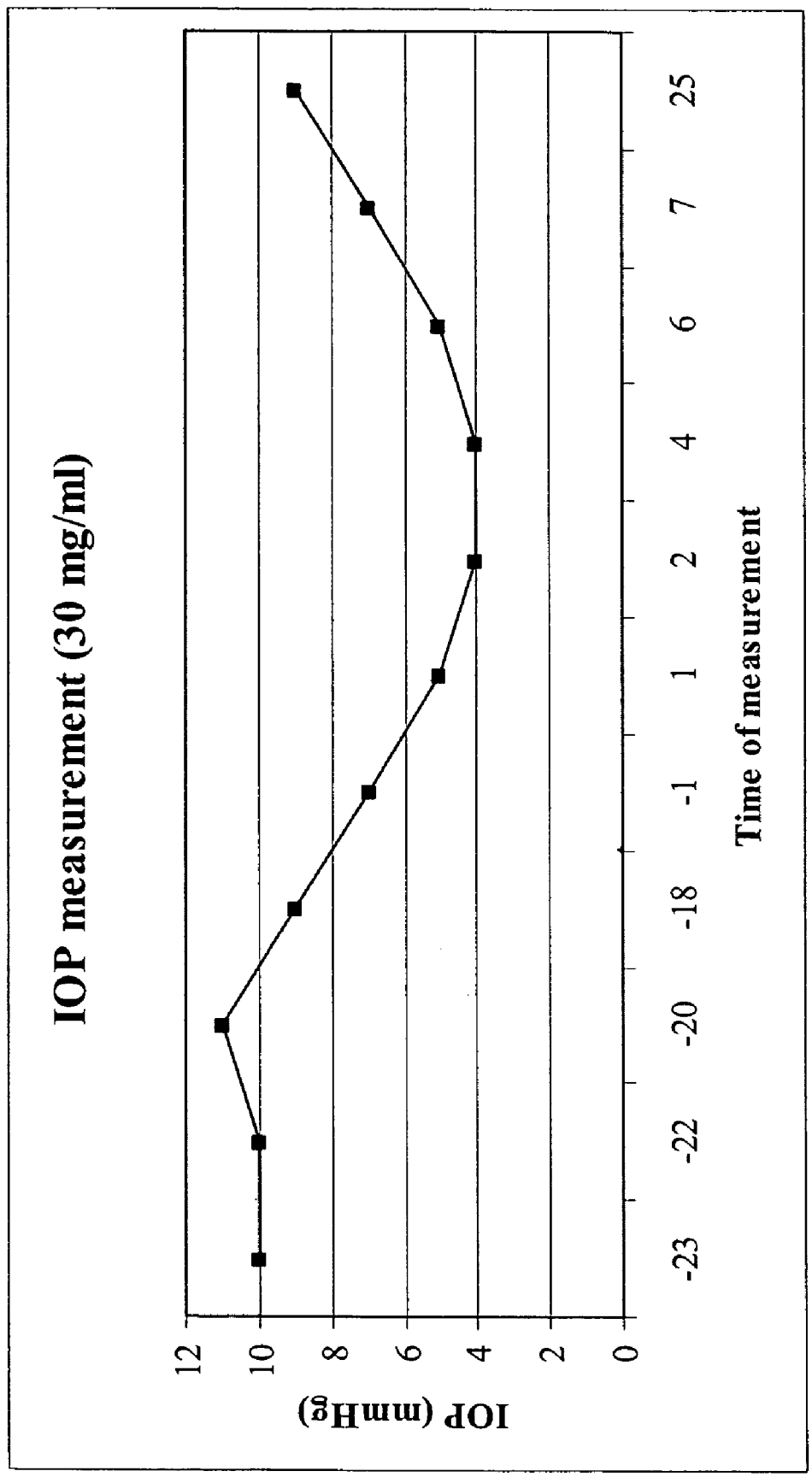

FIG. 1. depicts measured intraocular pressure in an adult New Zealand White rabbit, prior to (from −25 hours until 0 hours) and following treatment (until 25 hours after treatment) with 100 µL of 0.3 mg/mL of Compound I'-1;

FIG. 2. depicts measured intraocular pressure in an adult New Zealand White rabbit, prior to (from −25 hours until 0 hours) and following treatment (until 25 hours after treatment) with 100 µL of 1.0 mg/mL of Compound I'-1;

FIG. 3. depicts measured intraocular pressure in an adult New Zealand White rabbit, prior to (from −25 hours until 0 hours) and following treatment (until 25 hours after treatment) with 100 µL of 3.0 mg/mL of Compound I'-1;

FIG. 4. depicts measured intraocular pressure in an adult New Zealand White rabbit, prior to (from −25 hours until 0 hours) and following treatment (until 25 hours after treatment) with 100 µL of 10 mg/mL of Compound I'-1; and FIG. 5. depicts measured intraocular pressure in an adult New Zealand White rabbit, prior to (from −25 hours until 0 hours) and following treatment (until 25 hours after treatment) with 100 µL of 30 mg/mL of Compound I'-1.

4. DETAILED DESCRIPTION OF THE INVENTION

4.1 Definitions

The term "$C_1$-$C_{10}$ alkyl" as used herein refers to a straight or branched chain, saturated hydrocarbon having from 1 to 10 carbon atoms. Representative $C_1$-$C_{10}$ alkyl groups include, but are not limited to methyl, ethyl, propyl, isopropyl, butyl, sec-butyl, tert-butyl, pentyl, isopentyl, neopentyl, hexyl, isohexyl, neohexyl, heptyl, isoheptyl, neoheptyl, octyl, isooctyl, neooctyl, nonyl, isononyl, neononyl, decyl, isodecyl and neodecyl. In one embodiment, the $C_1$-$C_{10}$ alkyl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the $C_1$-$C_{10}$ alkyl is unsubstituted.

The term "$C_1$-$C_6$ alkyl" as used herein refers to a straight or branched chain, saturated hydrocarbon having from 1 to 6 carbon atoms. Representative $C_1$-$C_6$ alkyl groups include, but are not limited to methyl, ethyl, propyl, isopropyl, butyl, sec-butyl, tert-buty, pentyl, isopentyl, neopentyl, hexyl, isohexyl, and neohexyl.

The term "$C_2$-$C_6$ alkenyl" refers to a straight or branched chain hydrocarbon containing 2-6 carbon atoms and at least one double bond. Representative $C_2$-$C_6$ alkenyl groups include, but are not limited to, ethylene, propylene, 1-butylene, 2-butylene, isobutylene, sec-butylene, 1-pentene, 2-pentene, isopentene, 1-hexene, 2-hexene, 3-hexene and isohexene. In one embodiment, the $C_2$-$C_6$ alkenyl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the $C_2$-$C_6$ alkenyl group is unsubstituted.

The term "$C_2$-$C_6$ alkynyl" refers to a straight or branched chain hydrocarbon containing 2-6 carbon atoms and at least one triple bond. Representative $C_2$-$C_6$ alkynyl groups include, but are not limited to, acetylene, propyne, 1-butyne, 2-butyne, isobutyne, sec-butyne, 1-pentyne, 2-pentyne, isopentyne, 1-hexyne, 2-hexyne, 3-hexyne and isohexyne. In one embodiment, the $C_2$-$C_6$ alkynyl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the $C_2$-$C_6$ alkynyl group is unsubstituted.

The term "aryl" as used herein refers to a phenyl group or a naphthyl group. In one embodiment, the aryl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the aryl is unsubstituted.

The term "$C_3$-$C_8$ monocyclic cycloalkyl" as used herein is a 3-, 4-, 5-, 6-, 7- or 8-membered saturated non-aromatic monocyclic cycloalkyl ring. Representative $C_3$-$C_8$ monocyclic cycloalkyl groups include, but are not limited to, cyclopropyl, cyclobutyl, cyclopentyl, cyclohexyl, cycloheptyl and cyclooctyl. In one embodiment, the $C_3$-$C_8$ monocyclic cycloalkyl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the $C_3$-$C_8$ monocyclic cycloalkyl is unsubstituted.

The term "$C_3$-$C_8$ monocyclic cycloalkenyl" as used herein is a 3-, 4-, 5-, 6-, 7- or 8-membered non-aromatic monocyclic carbocyclic ring having at least one endocyclic double bond, but which is not aromatic. It is to be understood that when any two groups, together with the carbon atom to which they are attached form a $C_3$-$C_8$ monocyclic cycloalkenyl group, the carbon atom to which the two groups are attached remains tetravalent. Representative $C_3$-$C_8$ monocyclic cycloalkenyl groups include, but are not limited to, cyclopropenyl, cyclobutenyl, 1,3-cyclobutadienyl, cyclopentenyl, 1,3-cyclopentadienyl, cyclohexenyl, 1,3-cyclohexadienyl, cycloheptenyl, 1,3-cycloheptadienyl, 1,4-cycloheptadienyl, -1,3,5-cycloheptatrienyl, cyclooctenyl, 1,3-cyclooctadienyl, 1,4-cyclooctadienyl, -1,3,5-cyclooctatrienyl. In one embodiment, the $C_3$-$C_8$ monocyclic cycloalkenyl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —$C_1$-$C_6$ alkyl. Unless indicated, the $C_3$-$C_8$ monocyclic cycloalkenyl is unsubstituted.

The term "$C_8$-$C_{12}$ bicyclic cycloalkyl" as used herein is a 8-, 9-, 10-, 11- or 12-membered saturated, non-aromatic bicyclic cycloalkyl ring system. Representative $C_8$-$C_{12}$ bicyclic cycloalkyl groups include, but are not limited to, decahydronaphthalene, octahydroindene, decahydrobenzocycloheptene, and dodecahydroheptalene. In one embodiment, the $C_8$-$C_{12}$ bicyclic cycloalkyl group is substituted with one or more of the following groups: -halo, —O—($C_1$-$C_6$ alkyl), —OH, —CN, —COOR', —OC(O)R', —N(R')$_2$, —NHC(O)R' or —C(O)NHR' groups wherein each R' is independently —H or unsubstituted —C$_1$-C$_6$ alkyl. Unless indicated, the C$_8$-C$_{12}$ bicyclic cycloalkyl is unsubstituted.

The term "C$_8$-C$_{12}$ bicyclic cycloalkenyl" as used herein is a 8-, 9-, 10-, 11- or 12-membered non-aromatic bicyclic cycloalkyl ring system, having at least one endocyclic double bond. It is to be understood that when any two groups, together with the carbon atom to which they are attached form a C$_8$-C$_{12}$ bicyclic cycloalkenyl group, the carbon atom to which the two groups are attached remains tetravalent. Representative C$_8$-C$_{12}$ bicyclic cycloalkenyl groups include, but are not limited to, octahydronaphthalene, hexahydronaphthalene, hexahydroindene, tetrahydroindene, octahydrobenzocycloheptene, hexahydrobenzocycloheptene, tetrahydrobenzocycloheptene, decahydroheptalene, octahydroheptalene, hexahydroheptalene, and tetrahydroheptalene. In one embodiment, the C$_8$-C$_{12}$ bicyclic cycloalkyl group is substituted with one or more of the following groups: -halo, —O—(C$_1$-C$_6$ alkyl), —OH, —CN, —COOR', —OC(O)R', —N(R')$_2$, —NHC(O)R' or —C(O)NHR' groups wherein each R' is independently —H or unsubstituted —C$_1$-C$_6$ alkyl. Unless indicated, the C$_8$-C$_{12}$ bicyclic cycloalkenyl is unsubstituted.

The term "effective amount" as used herein refers to an amount of a Purine Derivative that is effective for: (i) treating or preventing a Condition; (ii) reducing an animal's core body temperature; or (iii) protecting an animal's heart against myocardial damage during cardioplegia.

The term "halo" as used herein refers to —F, —Cl, —Br or —I.

The term "3- to 7-membered monocyclic heterocycle" refers to: (i) a 3- or 4-membered non-aromatic monocyclic cycloalkyl in which 1 of the ring carbon atoms has been replaced with an N, O or S atom; or (ii) a 5-, 6-, or 7-membered aromatic or non-aromatic monocyclic cycloalkyl in which 1-4 of the ring carbon atoms have been independently replaced with a N, O or S atom. The non-aromatic 3- to 7-membered monocyclic heterocycles can be attached via a ring nitrogen, sulfur, or carbon atom. The aromatic 3- to 7-membered monocyclic heterocycles are attached via a ring carbon atom. Representative examples of a 3- to 7-membered monocyclic heterocycle group include, but are not limited to, furanyl, furazanyl, imidazolidinyl, imidazolinyl, imidazolyl, isothiazolyl, isoxazolyl, morpholinyl, oxadiazolyl, oxazolidinyl, oxazolyl, oxazolidinyl, pyrimidinyl, phenanthridinyl, phenanthrolinyl, piperazinyl, piperidinyl, pyranyl, pyrazinyl, pyrazolidinyl, pyrazolinyl, pyrazolyl, pyridazinyl, pyridooxazole, pyridoimidazole, pyridothiazole, pyridinyl, pyrimidinyl, pyrrolidinyl, pyrrolinyl, quinuclidinyl, tetrahydrofuranyl, thiadiazinyl, thiadiazolyl, thienyl, thienothiazolyl, thienooxazolyl, thienoimidazolyl, thiomorpholinyl, thiophenyl, triazinyl, triazolyl, In one embodiment, the 3- to 7-membered monocyclic heterocycle group is substituted with one or more of the following groups: -halo, —O—(C$_1$-C$_6$ alkyl), —OH, —CN, —COOR', —OC(O)R', —N(R')$_2$, —NHC(O)R' or —C(O)NHR' groups wherein each R' is independently —H or unsubstituted —C$_1$-C$_6$ alkyl. Unless indicated, the 3- to 7-membered monocyclic heterocycle is unsubstituted.

The term "8- to 12-membered bicyclic heterocycle" refers to a bicyclic 8- to 12-membered aromatic or non-aromatic bicyclic cycloalkyl in which one or both of the of the rings of the bicyclic ring system have 1-4 of its ring carbon atoms independently replaced with a N, O or S atom. Included in this class are 3- to 7-membered monocyclic heterocycles that are fused to a benzene ring. A non-aromatic ring of an 8- to 12-membered monocyclic heterocycle is attached via a ring nitrogen, sulfur, or carbon atom. An aromatic 8- to 12-membered-monocyclic heterocycle is attached via a ring carbon atom. Examples of 8- to 12-membered bicyclic heterocycles include, but are not limited to, benzimidazolyl, benzofuranyl, benzothiofuranyl, benzothiophenyl, benzoxazolyl, benzthiazolyl, benztriazolyl, benztetrzolyl, benzisoxazolyl, benzisothiazolyl, benzimidazolinyl, cinnolinyl, decahydroquinolinyl, 1H-indazolyl, indolenyl, indolinyl, indolizinyl, indolyl, isobenzofuranyl, isoindazolyl, isoindolyl, isoindolinyl, isoquinolinyl, naphthyridinyl, octahydroisoquinolinyl, phthalazinyl, pteridinyl, purinyl, quinoxalinyl, tetrahydroisoquinolinyl, tetrahydroquinolinyl, and xanthenyl. In one embodiment, each ring of the 8- to 12-membered bicyclic heterocycle group can substituted with one or more of the following groups: -halo, —O—(C$_1$-C$_6$ alkyl), —OH, —CN, —COOR', —OC(O)R', —N(R')$_2$, —NHC(O)R' or —C(O)NHR' groups wherein each R' is independently —H or unsubstituted —C$_1$-C$_6$ alkyl. Unless indicated, the 8- to 12-membered bicyclic heterocycle is unsubstituted.

The phrase "pharmaceutically acceptable salt," as used herein, is a salt of an acid and a basic nitrogen atom of a Purine Derivative. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The pharmaceutically acceptable salt can also be a camphorsulfonate salt. The term "pharmaceutically acceptable salt" also refers to a salt of a Purine Derivative having an acidic functional group, such as a carboxylic acid functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl)amine; N-methyl-D-glucamine; and amino acids such as arginine, lysine, and the like. The term "pharmaceutically acceptable salt" also includes a hydrate of a Purine Derivative.

An "animal" is a mammal, e.g., a human, mouse, rat, guinea pig, dog, cat, horse, cow, pig, or non-human primate, such as a monkey, chimpanzee or baboon. In one embodiment, a monkey is a rhesus. In another embodiment, an animal is a human.

The term "isolated and purified" as used herein means separate from other components of a reaction mixture or natural source. In certain embodiments, the isolate contains at least 30%, at least 35%, at least 40%, at least 45%, at least 50%, at least 55%, at least 60%, at least 65%, at least 70%, at least 75%, at least 80%, at least 85%, at least 90%, at least 95% or at least 98% of a Purine Derivative by weight of the isolate. In one embodiment, the isolate contains at least 95% of a Purine Derivative by weight of the isolate.

The term "substantially free of its corresponding opposite enantiomer" as used herein, means that a Purine Derivative contains no more than about 10% by weight of its corresponding opposite enantiomer. In one embodiment the Purine Derivative that is substantially free of its corresponding opposite enantiomer contains no more than about 5% by weight of its corresponding opposite enantiomer. In a further embodiment a Purine Derivative that is substantially free of its corresponding opposite enantiomer contains no more than about 1% by weight of its corresponding opposite enantiomer. In another embodiment a Purine Derivative that is substantially free of its corresponding opposite enantiomer contains no more than about 0.5% by weight of its corresponding opposite enantiomer. In still another embodiment a Purine Derivative that is substantially free of its corresponding opposite enantiomer contains no more than about 0.1% by weight of its corresponding opposite enantiomer.

The term "substantially free of its corresponding other anomer" as used herein, means that a Purine Derivative contains no more than about 10% by weight of its corresponding other anomer. In one embodiment the Purine Derivative that is substantially free of its corresponding other anomer contains no more than about 5% by weight of its corresponding other anomer. In a further embodiment a Purine Derivative that is substantially free of its corresponding other anomer contains no more than about 1% by weight of its corresponding other anomer. In another embodiment a Purine Derivative that is substantially free of its corresponding other anomer contains no more than about 0.5% by weight of its corresponding other anomer. In still another embodiment a Purine Derivative that is substantially free of its corresponding other anomer contains no more than about 0.1% by weight of its corresponding other anomer.

Some chemical structures herein are depicted using bold and dashed lines to represent chemical bonds. These bold and dashed lines depict absolute stereochemistry. A bold line indicates that a substituent is above the plane of the carbon atom to which it is attached and a dashed line indicates that a substituent is below the plane of the carbon atom to which it is attached. For example, in the illustration below:

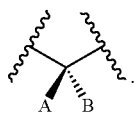

group A is above the plane of the carbon atom to which it is attached and group B is below the plane of the carbon atom to which it is attached.

It is to be understood that in group D of the Purine Derivatives of Formula (I), depicted below:

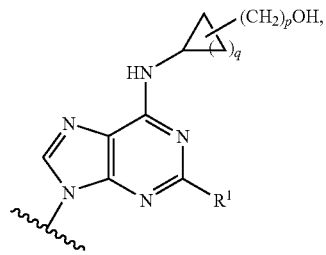

the —$(CH_2)_p$OH group can be joined at any carbon atom of the

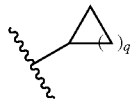

group to which it is attached.

The following abbreviations are used herein and have the indicated definitions: ATP is adenosine triphosphate; CCPA is 2-chloro-$N^6$-cyclopentyladenosine; CPA is $N^6$-cyclopentyladenosine; CHO is chinese hamster ovary; Et is ethyl; EtOH is ethanol; HEK is human embryonic kidney; LiHMDS is lithium hexamethyldisilazide; MeOH is methanol; MS is mass spectrometry; NECA is adenosine-5'-(N-ethyl)carboxamido; NMR is nuclear magnetic resonance; Ph is phenyl; R-PIA is $N^6$-(2-phenyl-isopropyl) adenosine, R-isomer; TFA is trifluoroacetic acid; THF is tetrahydrofuran; TMSOTf is trimethylsilyl trifluoromethanesulfonate.

4.2 The Purine Derivatives

4.2.1 The Purine Derivatives of Formula (I)

As stated above, the present invention encompasses Purine Derivatives having the Formula (I):

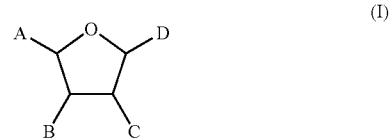

wherein A, B, C and D are defined above for the Purine Derivatives of Formula (I), and A and B are trans with respect to each other; B and C are cis with respect to each other; and C and D are cis or trans with respect to each other.

In one embodiment, $R^1$ is —H.
In another embodiment, $R^1$ is -halo.
In a specific embodiment, $R^1$ is —Cl.
In another embodiment, $R^1$ is —CN.
In still another embodiment, $R^1$ is —N($R^2$)$_2$.
In yet another embodiment, $R^1$ is —O$R^2$.
In a further embodiment, $R^1$ is —S$R^2$.
In another embodiment, $R^1$ is —NHC(O)O$R^2$, —NHC(O)$R^2$, or —NHC(O)N($R^2$)$_2$.
In another embodiment, $R^1$ is —C(O)O$R^2$, —C(O)$R^2$, —C(O)N($R^2$)$_2$, or —OC(O)N($R^2$)$_2$.
In still another embodiment, $R^1$ is $CF_3$.
In yet another embodiment, $R^1$ is —$NO_2$.
In one embodiment, p is 1.
In another embodiment, p is other than 1.
In one embodiment, q is 1.
In another embodiment, q is 2.
In still another embodiment, q is 3.
In yet another embodiment, q is 4.
In yet another embodiment, q is 3 or 4.
In a further embodiment, q is 5.
In another embodiment, q is 6.
In one embodiment, $R^1$ is —H, p is 1 and q is 1.
In another embodiment, $R^1$ is -halo, p is 1 and q is 1.
In still another embodiment, $R^1$ is —Cl, p is 1 and q is 1.

In still another embodiment, $R^1$ is —H or -halo and q is 3 or 4.

In still another embodiment, $R^1$ is —H or -halo, q is 3 or 4 and p is 1.

In still another embodiment, $R^1$ is —H or —Cl, q is 3 or 4 and p is 1.

In one embodiment, C and D are cis with respect to each other.

In another embodiment, C and D are trans with respect to each other.

The present invention also provides compositions comprising an effective amount of a Purine Derivative of Formula (I) and a physiologically acceptable carrier or vehicle.

The invention further provides Purine Derivatives of Formula (I) that are in isolated and purified form.

The invention still further provides methods for treating or preventing a Condition, comprising administering an effective amount of a Purine Derivative of Formula (I) to an animal in need thereof.

The invention further provides methods for reducing an animal's core body temperature, comprising administering an effective amount of a Purine Derivative of Formula (I) to an animal in need thereof.

The invention further provides methods for protecting an animal's heart against myocardial damage during cardioplegia, comprising administering an effective amount of a Purine Derivative of Formula (I) to an animal in need thereof.

The Purine Derivatives of Formula (I) can exist in the form of a single enantiomer, for example, that depicted by either the Formula (Ia') or Formula (Ia"):

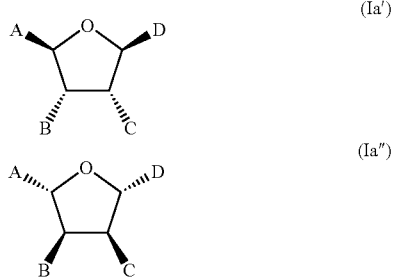

wherein A, B, C and D are defined above for the Purine Derivatives of Formula (I).

A Purine Derivative of Formula (Ia') is the corresponding opposite enantiomer of a Purine Derivative of Formula (Ia") when group A of the Purine Derivative of Formula (Ia') is the same as group A of the Purine Derivative of Formula (Ia") and when group D of the Purine Derivative of Formula (Ia') is the same as group D of the Purine Derivative of Formula (Ia").

A Purine Derivative of Formula (Ia") is the corresponding opposite enantiomer of a Purine Derivative of Formula (Ia') when group A of the Purine Derivative of Formula (Ia") is the same as group A of the Purine Derivative of Formula (Ia') and when group D of the Purine Derivative of Formula (Ia") is the same as group D of the Purine Derivative of Formula (Ia').

In one embodiment, the Purine Derivatives of Formula (I) have the formula (Ia'), depicted above, wherein A, B, C and D are defined above for the Purine Derivatives of Formula (I), and wherein the Purine Derivatives of Formula (Ia') are substantially free of their corresponding opposite enantiomer.

In another embodiment, the Purine Derivatives of Formula (I) have the formula (Ia"), depicted above, wherein A, B, C and D are defined above for the Purine Derivatives of Formula (I), and wherein the Purine Derivatives of Formula (Ia") are substantially free of their corresponding opposite enantiomer.

In another embodiment, the Purine Derivatives of Formula (I) exist as a mixture of a Purine Derivative of Formula (Ia') and a Purine Derivative of Formula (Ia") wherein the amount of the Purine Derivative of Formula (Ia') exceeds the amount of the Purine Derivative of Formula (Ia").

In a further embodiment, the Purine Derivatives of Formula (I) exist as a mixture of a Purine Derivative of Formula (Ia') and a Purine Derivative of Formula (Ia") wherein the amount of the Purine Derivative of Formula (Ia") exceeds the amount of the Purine Derivative of Formula (Ia').

In another embodiment, the Purine Derivatives of Formula (I) exist as a racemic mixture of a Purine Derivative of Formula (Ia') and a Purine Derivative of Formula (Ia").

In another embodiment, the Purine Derivatives of Formula (I) can exist in the form of a single enantiomer, for example, that depicted by either formula (Iaa') or (Iaa"):

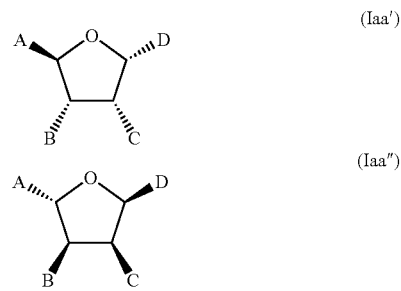

wherein A, B, C and D are defined above for the Purine Derivatives of Formula (I).

A Purine Derivative of Formula (Iaa') is the corresponding opposite enantiomer of a Purine Derivative of Formula (Iaa") when group A of the Purine Derivative of Formula (Iaa') is the same as group A of the Purine Derivative of Formula (Iaa") and when group D of the Purine Derivative of Formula (Iaa') is the same as group D of the Purine Derivative of Formula (Iaa").

A Purine Derivative of Formula (Iaa") is the corresponding opposite enantiomer of a Purine Derivative of Formula (Iaa') when group A of the Purine Derivative of Formula (Iaa") is the same as group A of the Purine Derivative of Formula (Iaa') and when group D of the Purine Derivative of Formula (Iaa") is the same as group D of the Purine Derivative of Formula (Iaa').

In one embodiment, the Purine Derivatives of Formula (I) have the formula (Iaa'), depicted above, wherein A, B, C and D are defined above for the Purine Derivatives of Formula (I), and wherein the Purine Derivatives of Formula (Iaa') are substantially free of their corresponding opposite enantiomer.

In another embodiment, the Purine Derivatives of Formula (I) have the formula (Iaa"), depicted above, wherein A, B, C and D are defined above for the Purine Derivatives of Formula (I), and wherein the Purine Derivatives of Formula (Iaa") are substantially free of their corresponding opposite enantiomer.

In another embodiment, the Purine Derivatives of Formula (I) exist as a mixture of a Purine Derivative of Formula (Iaa') and a Purine Derivative of Formula (Iaa") wherein the amount of the Purine Derivative of Formula (Iaa') exceeds the amount of the Purine Derivative of Formula (Iaa").

In a further embodiment, the Purine Derivatives of Formula (I) exist as a mixture of a Purine Derivative of Formula (Iaa') and a Purine Derivative of Formula (Iaa") wherein the amount of the Purine Derivative of Formula (Iaa") exceeds the amount of the Purine Derivative of Formula (Iaa').

In another embodiment, the Purine Derivatives of Formula (I) exist as a racemic mixture of a Purine Derivative of Formula (Iaa') and a Purine Derivative of Formula (Iaa").

A Purine Derivative of Formula (Iaa') is the corresponding other anomer of a Purine Derivative of Formula (Ia') when group A of the Purine Derivative of Formula (Iaa') is the same as group A of the Purine Derivative of Formula (Ia') and when group D of the Purine Derivative of Formula (Iaa') is the same as group D of the Purine Derivative of Formula (Ia').

A Purine Derivative of Formula (Ia') is the corresponding other anomer of a Purine Derivative of Formula (Iaa') when group A of the Purine Derivative of Formula (Ia') is the same as group A of the Purine Derivative of Formula (Iaa') and when group D of the Purine Derivative of Formula (Ia') is the same as group D of the Purine Derivative of Formula (Iaa').

A Purine Derivative of Formula (Iaa") is the corresponding other anomer of a Purine Derivative of Formula (Ia") when group A of the Purine Derivative of Formula (Iaa") is the same as group A of the Purine Derivative of Formula (Ia") and when group D of the Purine Derivative of Formula (Iaa") is the same as group D of the Purine Derivative of Formula (Ia").

A Purine Derivative of Formula (Ia") is the corresponding other anomer of a Purine Derivative of Formula (Iaa") when group A of the Purine Derivative of Formula (Ia") is the same as group A of the Purine Derivative of Formula (Iaa") and when group D of the Purine Derivative of Formula (Ia") is the same as group D of the Purine Derivative of Formula (Iaa").

In one embodiment, the Purine Derivatives of Formula (I) have the formula (Iaa'), depicted above, wherein A, B, C and D are defined above for the Purine Derivatives of Formula (I), and wherein the Purine Derivatives of Formula (Iaa') are substantially free of their corresponding other anomer.

In another embodiment, the Purine Derivatives of Formula (I) have the formula (Iaa"), depicted above, wherein A, B, C and D are defined above for the Purine Derivatives of Formula (I), and wherein the Purine Derivatives of Formula (Iaa") are substantially free of their corresponding other anomer.

In one embodiment, the Purine Derivatives of Formula (I) have the formula (Ia'), depicted above, wherein A, B, C and D are defined above for the Purine Derivatives of Formula (I), and wherein the Purine Derivatives of Formula (Ia') are substantially free of their corresponding other anomer.

In another embodiment, the Purine Derivatives of Formula (I) have the formula (Ia"), depicted above, wherein A, B, C and D are defined above for the Purine Derivatives of Formula (I), and wherein the Purine Derivatives of Formula (Ia") are substantially free of their corresponding other anomer.

In one embodiment, the Purine Derivatives of Formula (I) exist as a mixture of a Purine Derivative of Formula (Ia') and a Purine Derivative of Formula (Iaa') wherein the amount of the Purine Derivative of Formula (Ia') exceeds the amount of the Purine Derivative of Formula (Iaa').

In another embodiment, the Purine Derivatives of Formula (I) exist as a mixture of a Purine Derivative of Formula (Ia') and a Purine Derivative of Formula (Iaa') wherein the amount of the Purine Derivative of Formula. (Iaa') exceeds the amount of the Purine Derivative of Formula (Ia').

In a further embodiment, the Purine Derivatives of Formula (I) exist as a equal mixture of a Purine Derivative of Formula (Ia') and a Purine Derivative of Formula (Iaa').

In one embodiment, the Purine Derivatives of Formula (I) exist as a mixture of a Purine Derivative of Formula (Ia") and a Purine Derivative of Formula (Iaa") wherein the amount of the Purine Derivative of Formula (Ia") exceeds the amount of the Purine Derivative of Formula (Iaa").

In another embodiment, the Purine Derivatives of Formula (I) exist as a mixture of a Purine Derivative of Formula (Ia") and a Purine Derivative of Formula (Iaa") wherein the amount of the Purine Derivative of Formula (Iaa") exceeds the amount of the Purine Derivative of Formula (Ia").

In a further embodiment, the Purine Derivatives of Formula (I) exist as a equal mixture of a Purine Derivative of Formula (Ia") and a Purine Derivative of Formula (Iaa").

Illustrative Purine Derivatives of Formula (I) include the compounds of formula (I') as set forth below:

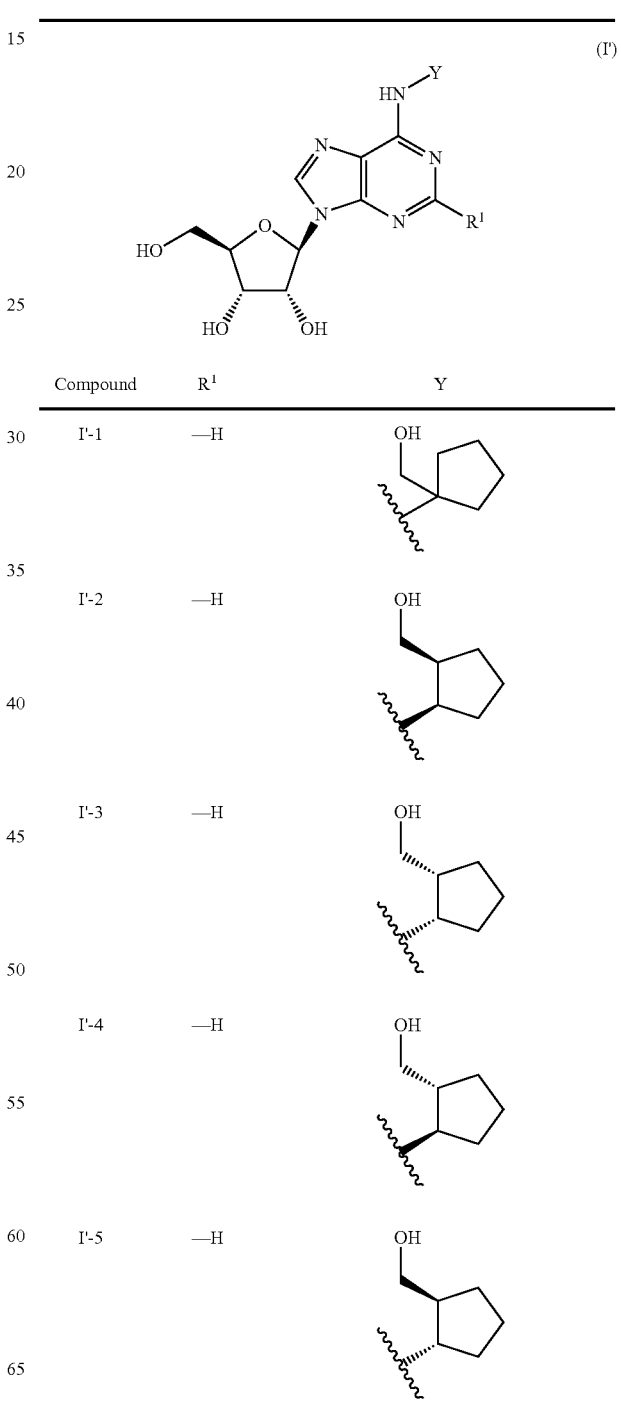

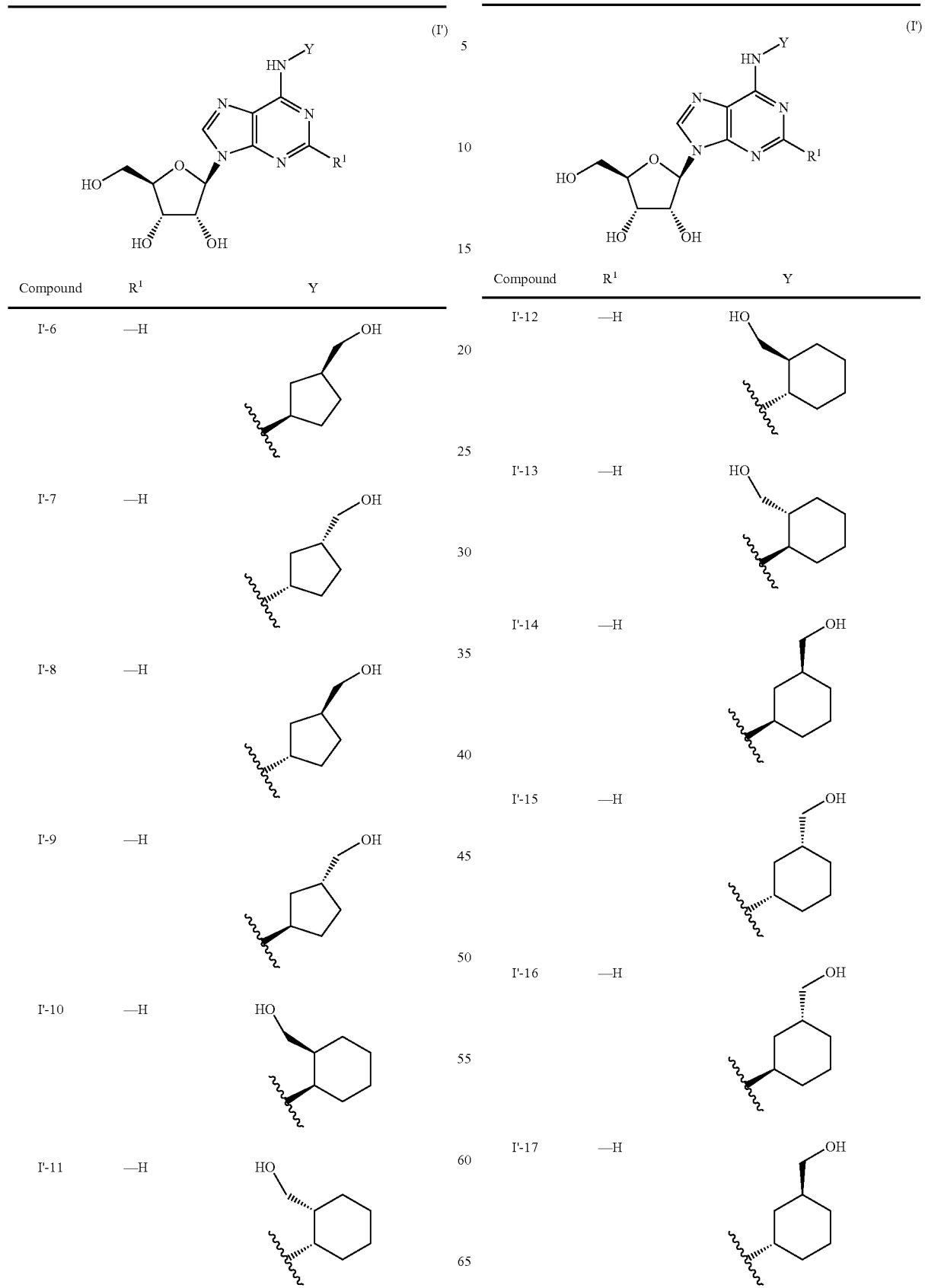

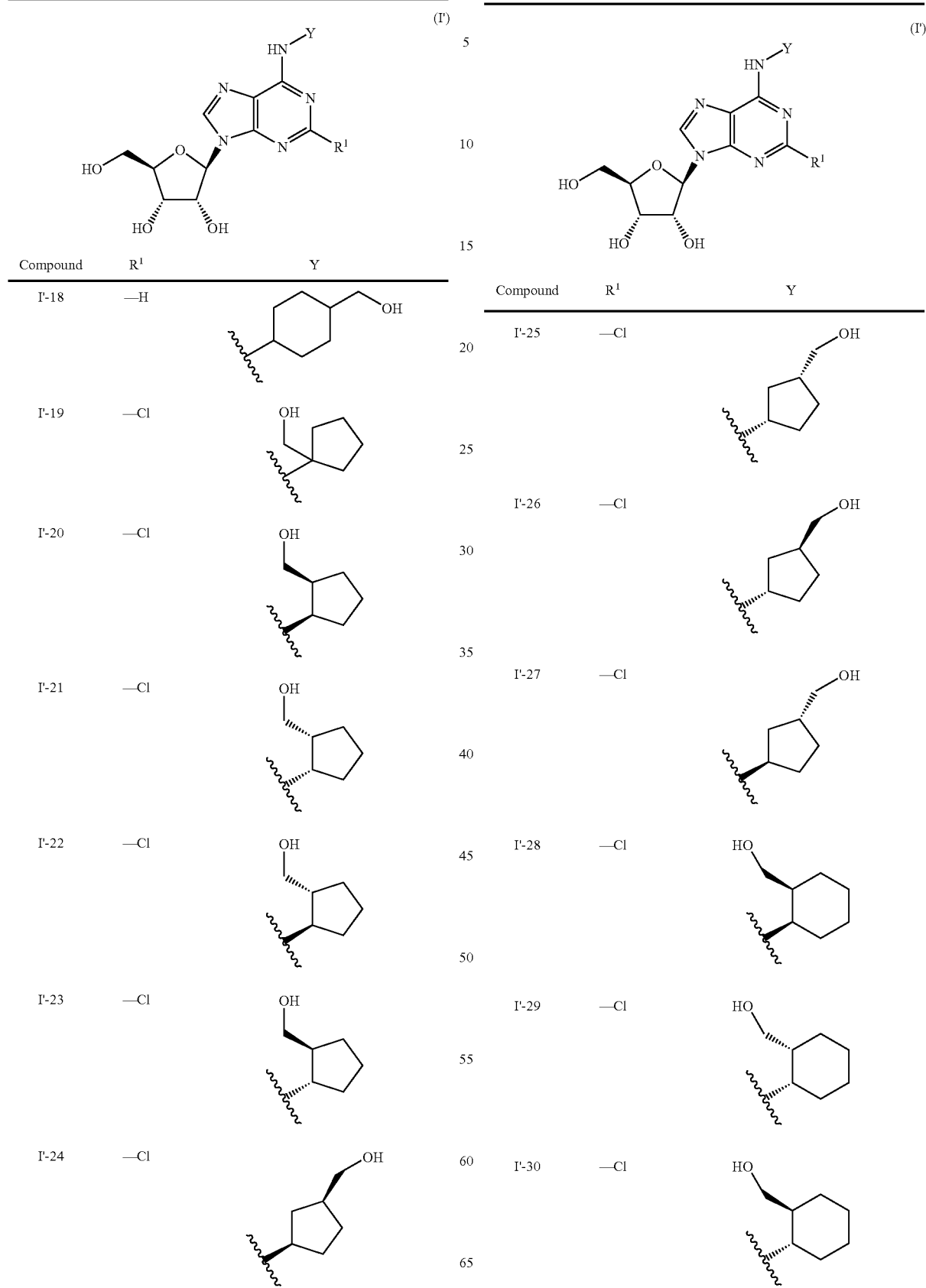

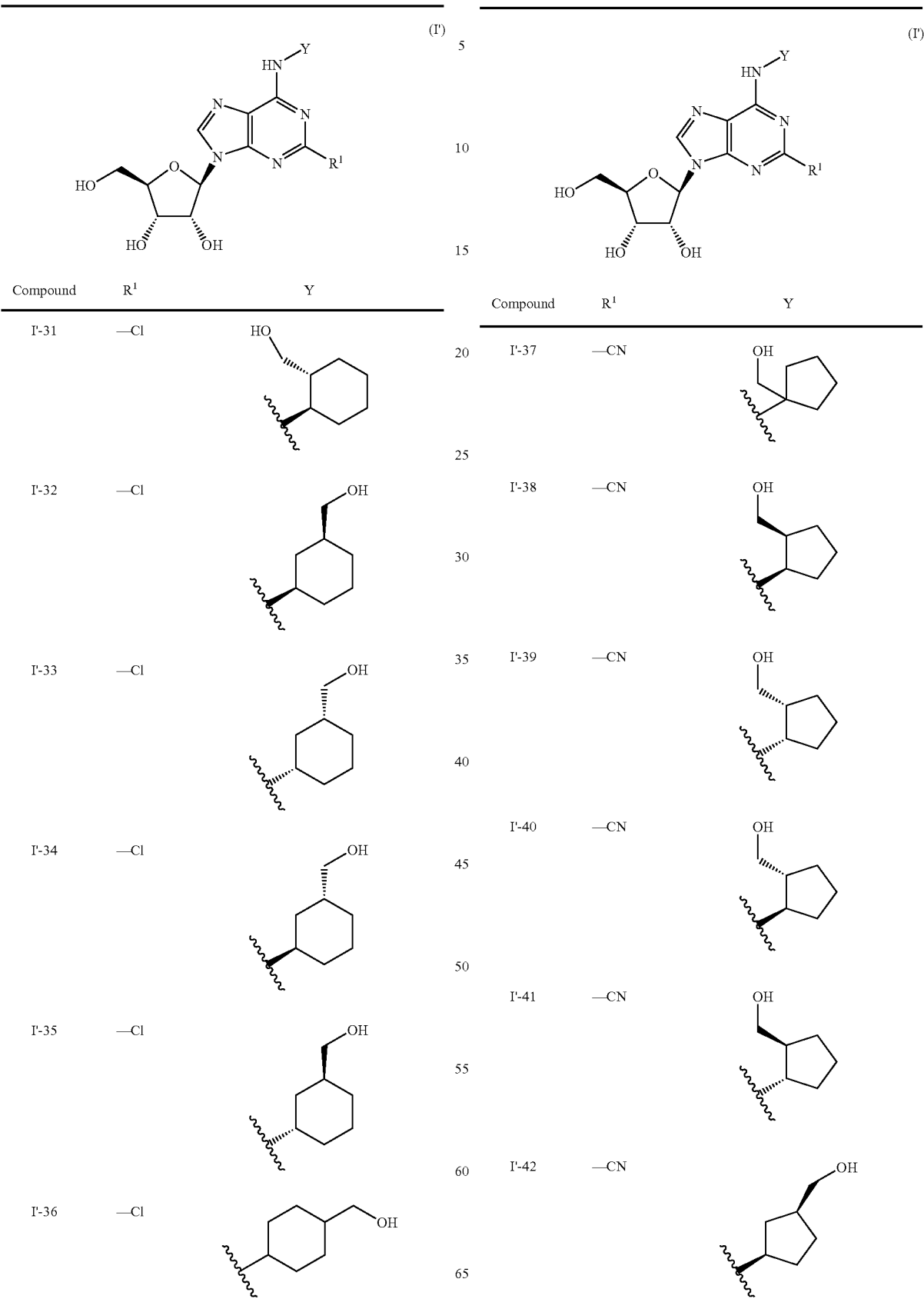

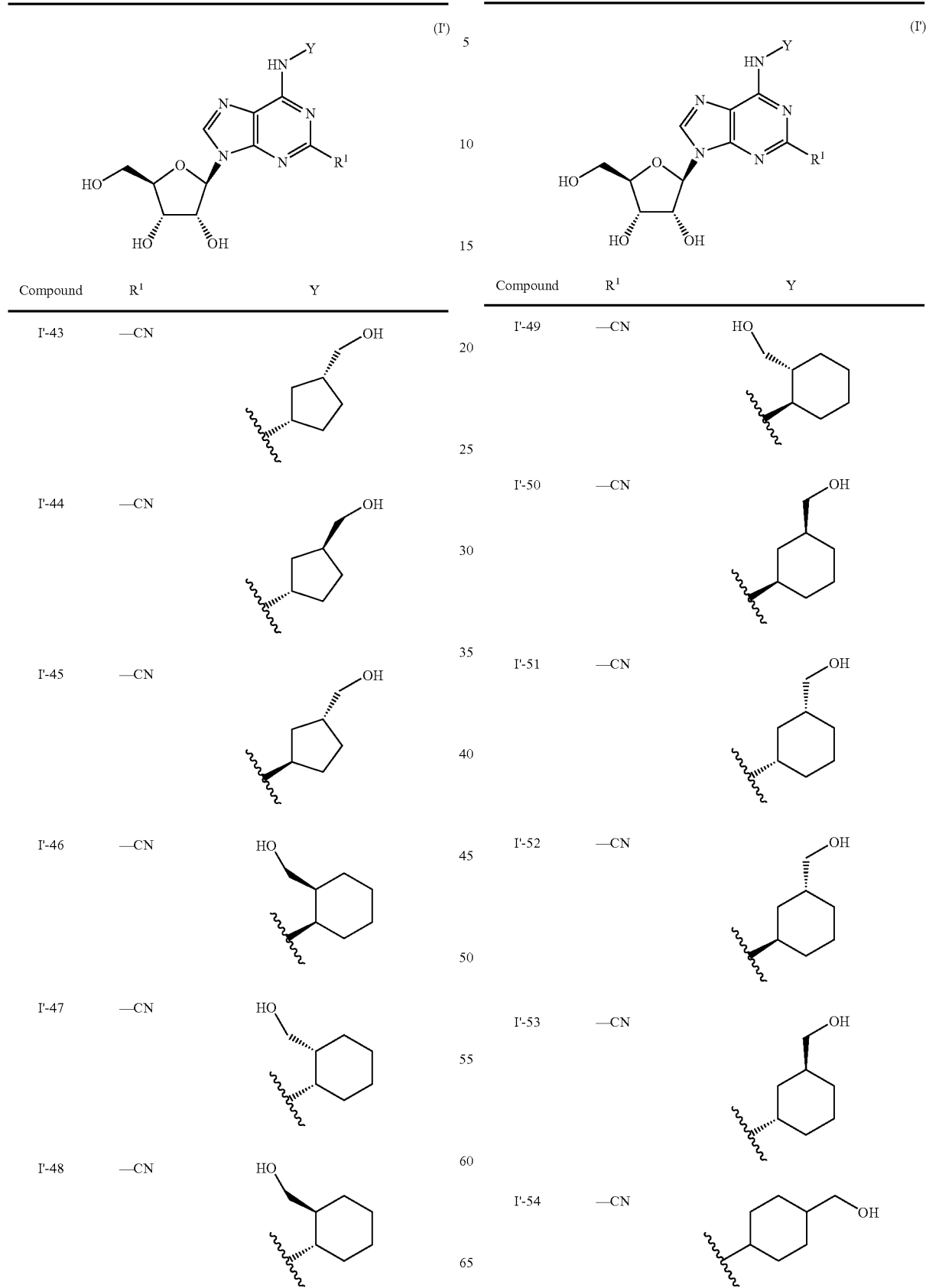

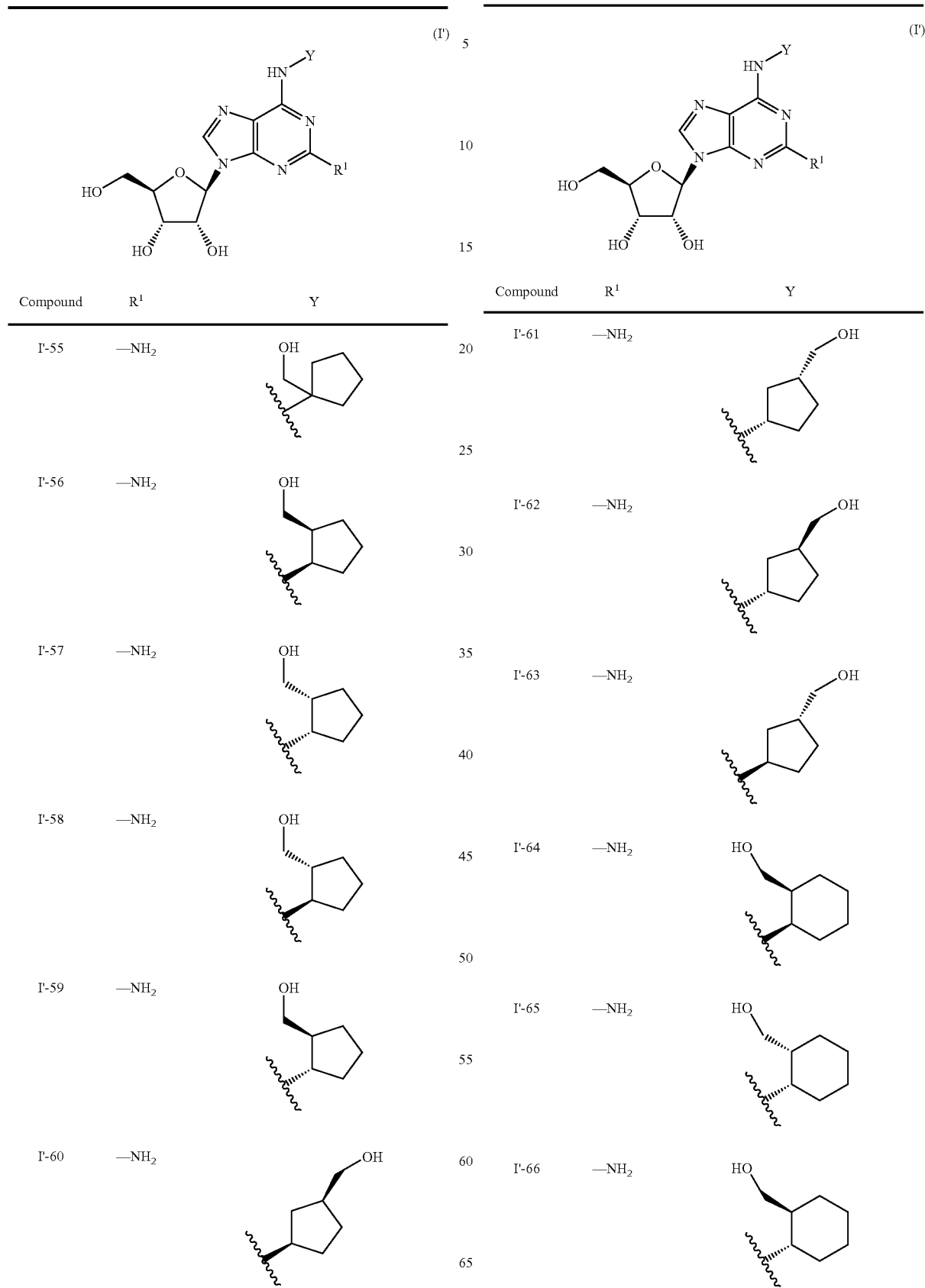

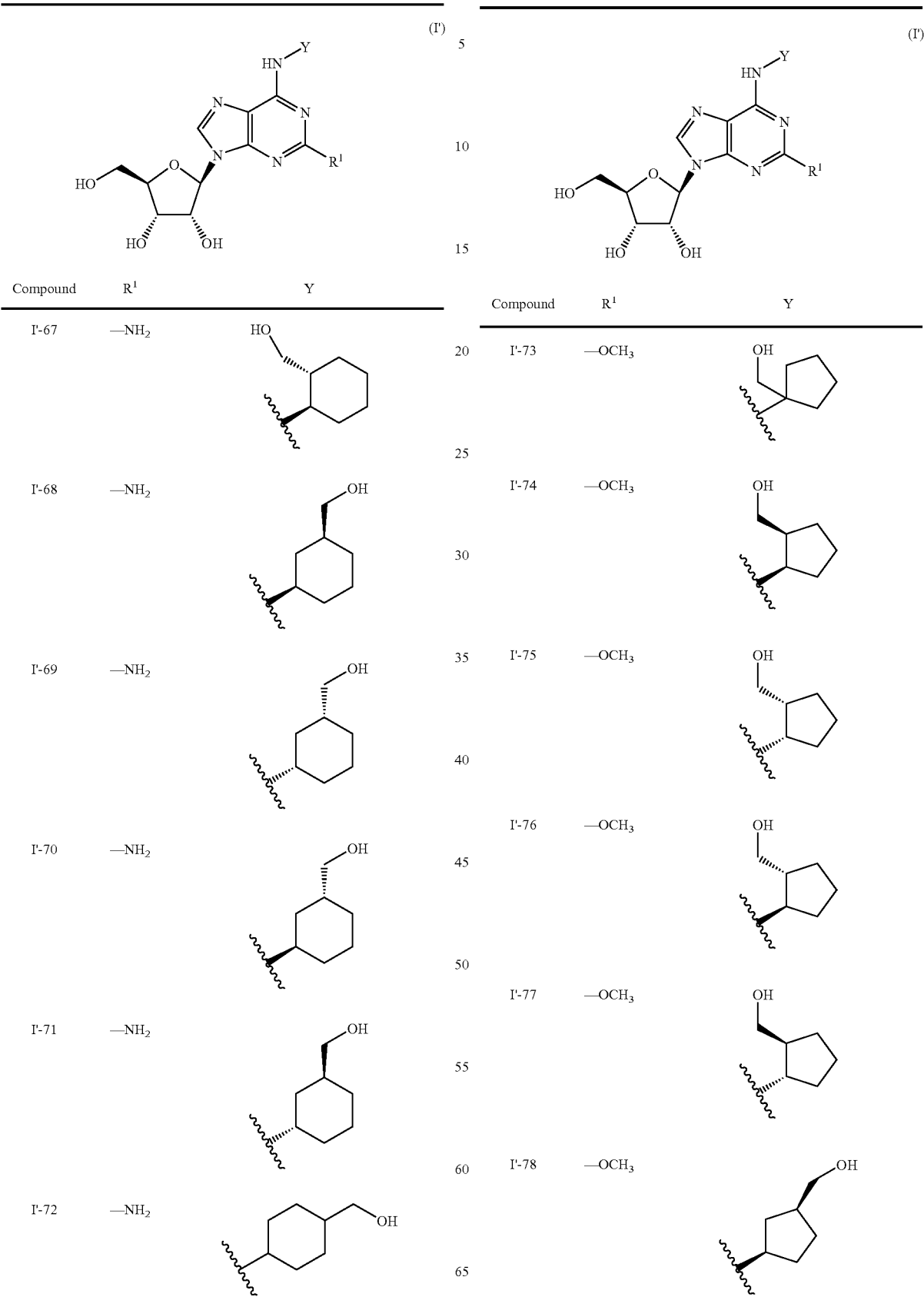

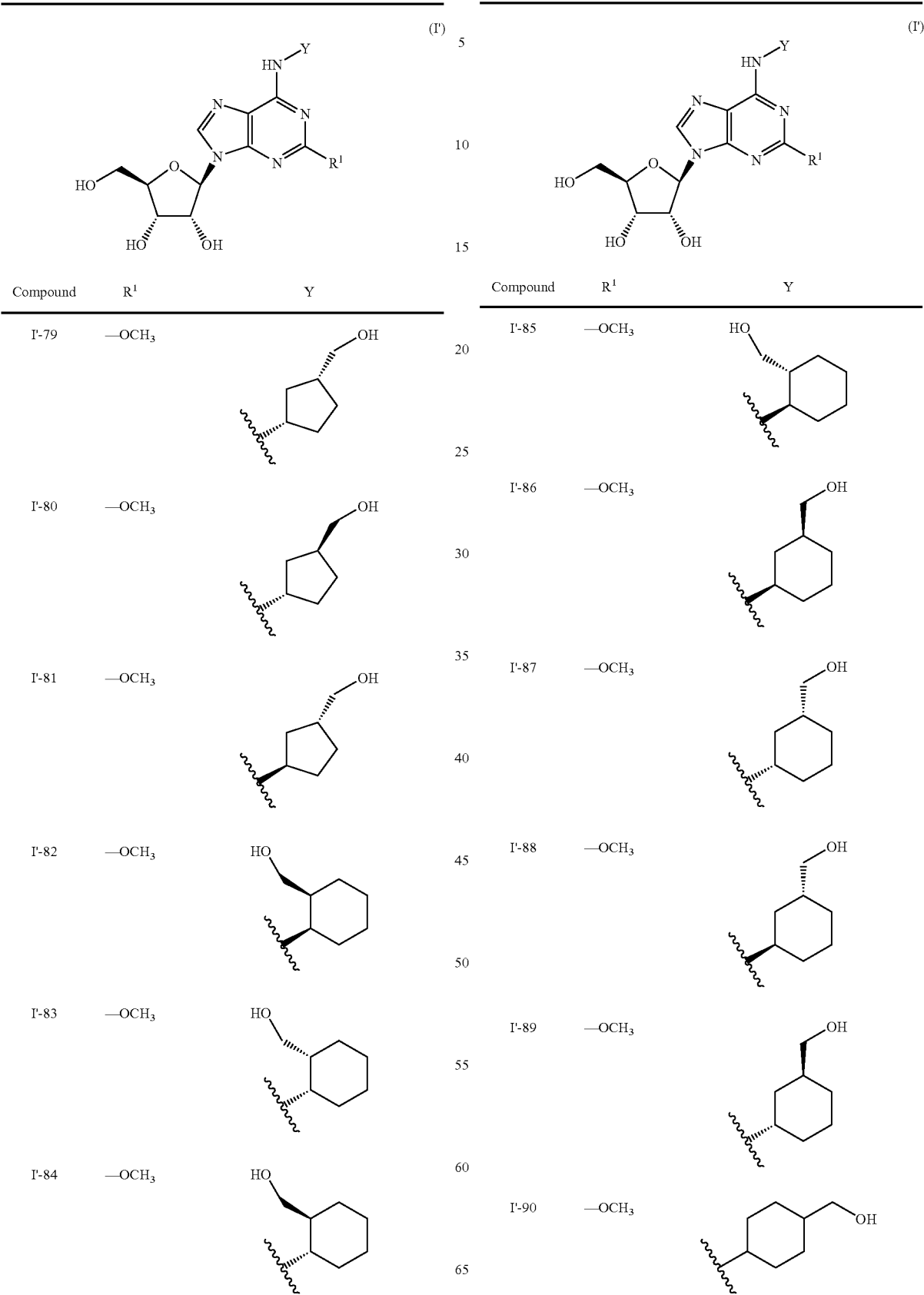

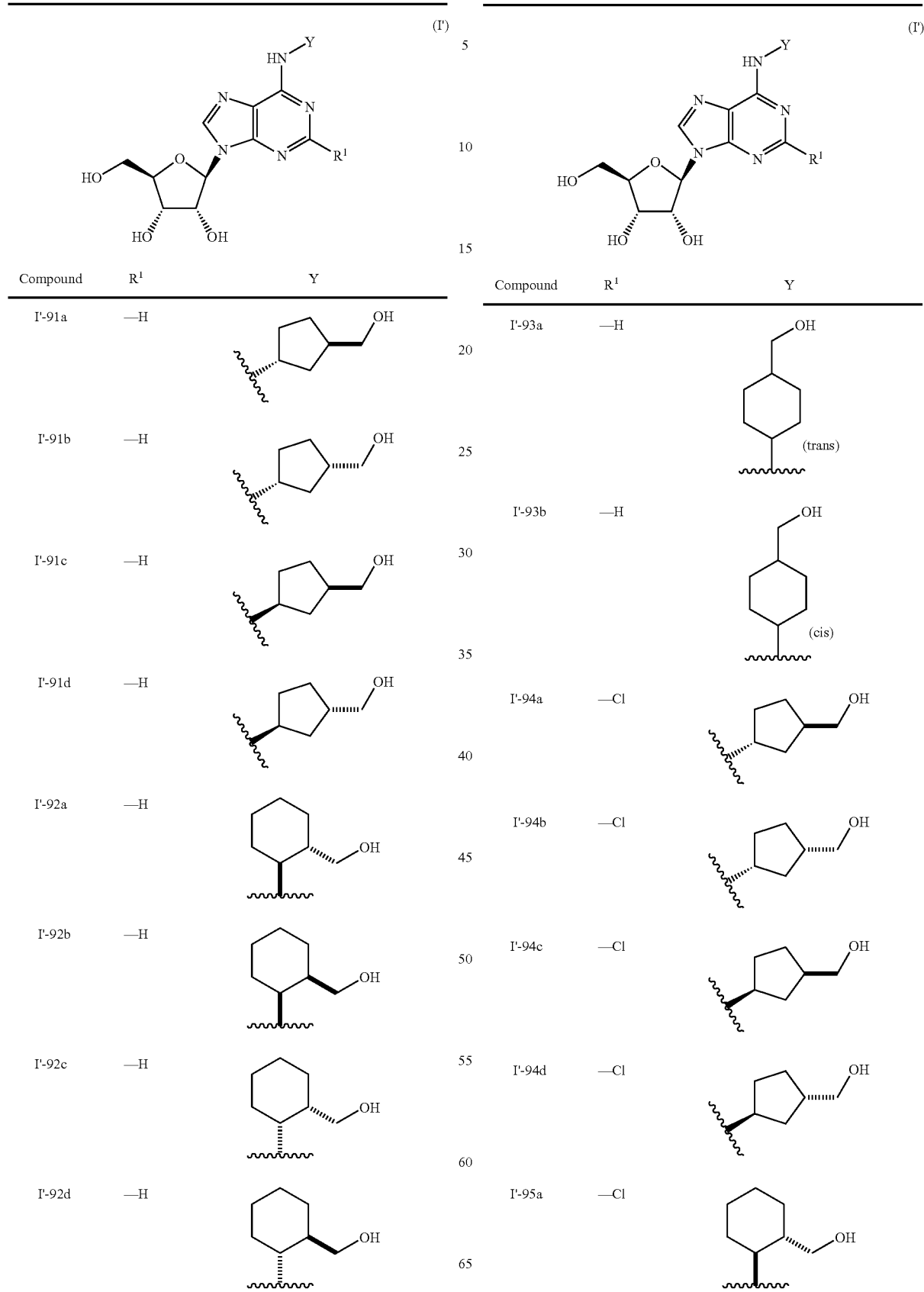

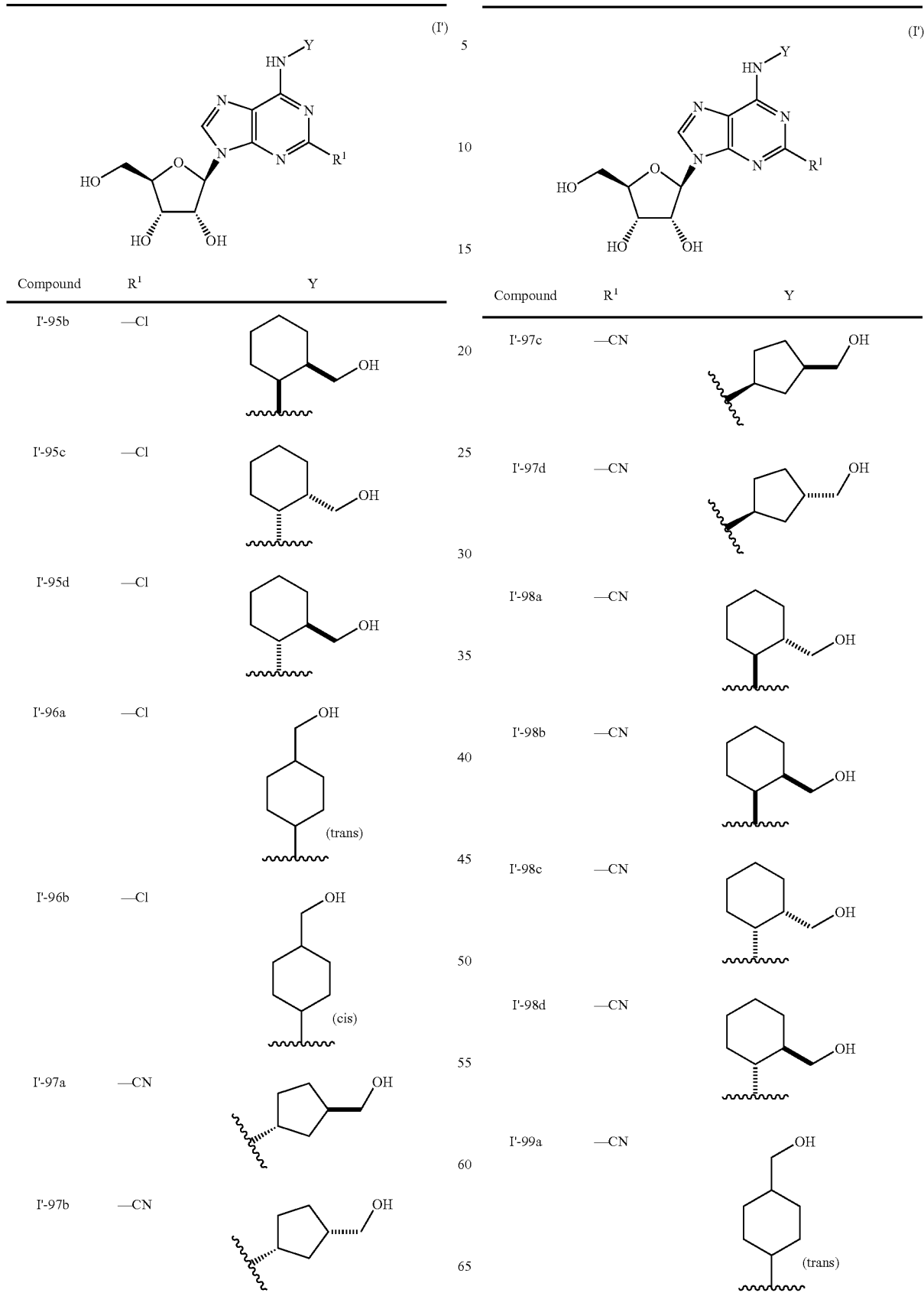

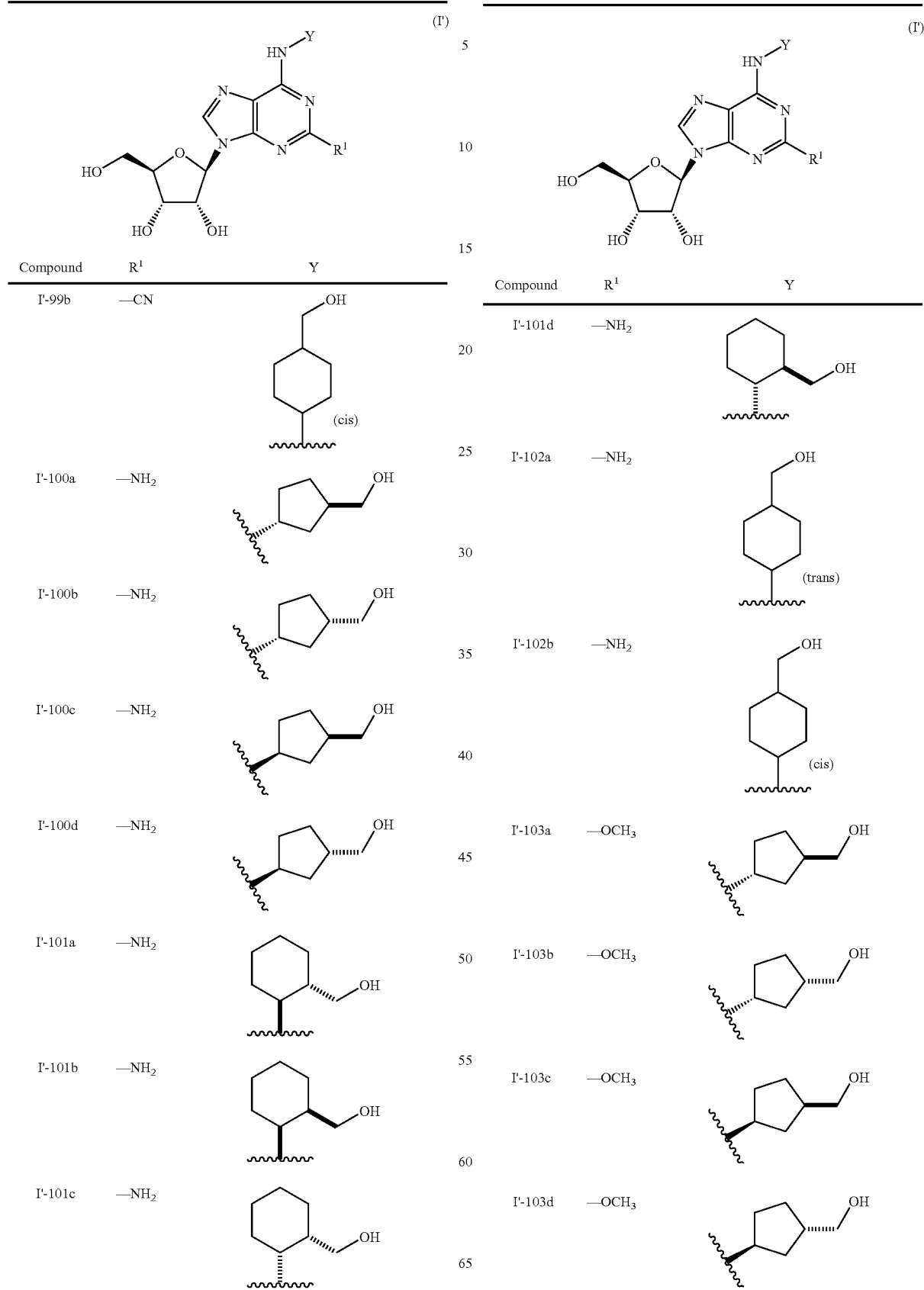

-continued
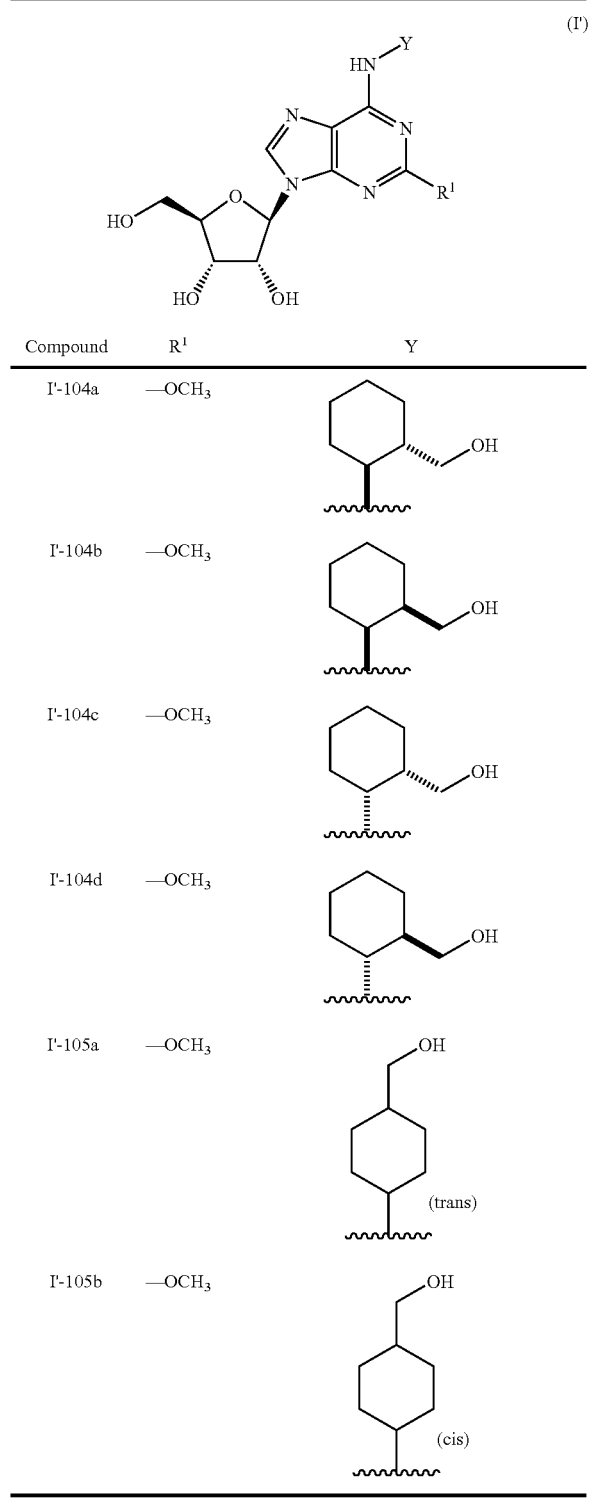
or a pharmaceutically acceptable salt thereof.
4.3 Methods for Making the Purine Derivatives
The Purine Derivatives can be made using the synthetic procedures outlined below in Schemes 1-5.
Scheme 1 shows methods for making specific stereoisomeric 6-chloroadenosine intermediates that are useful for making the Purine Derviatives of Formula (I).
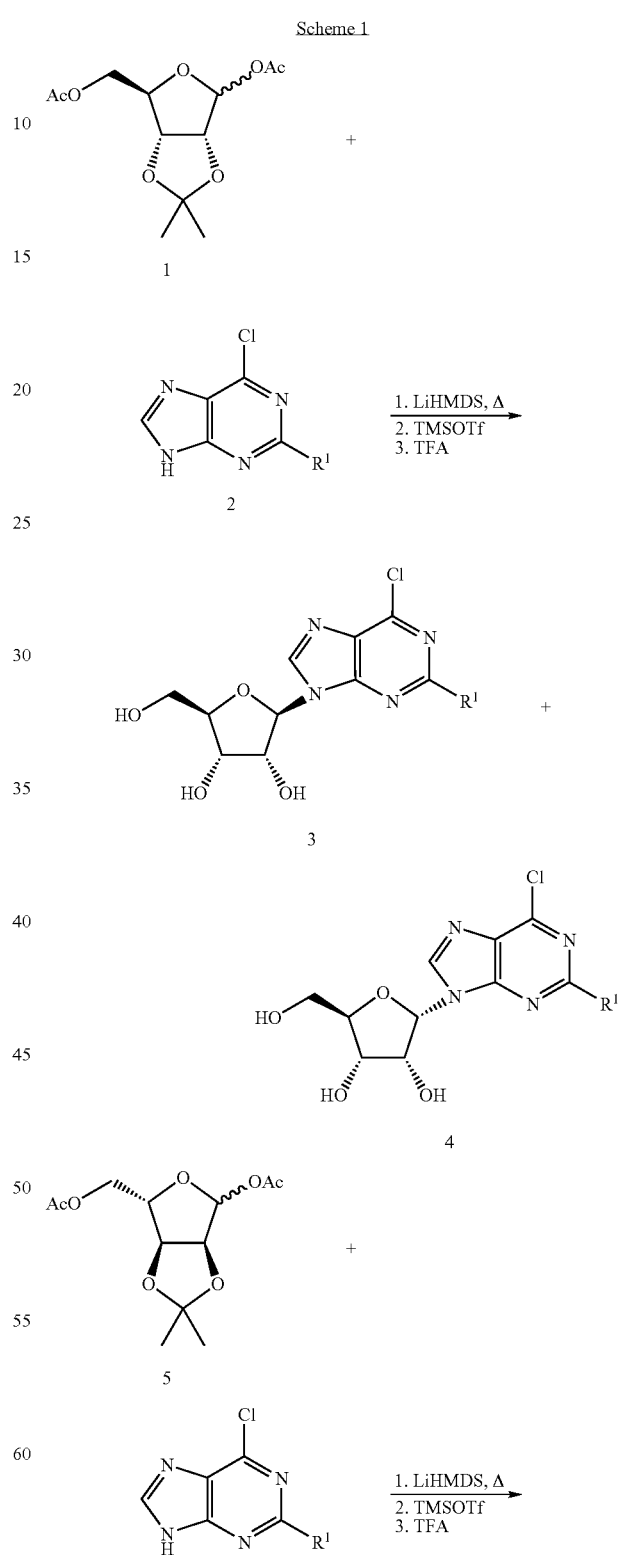

-continued

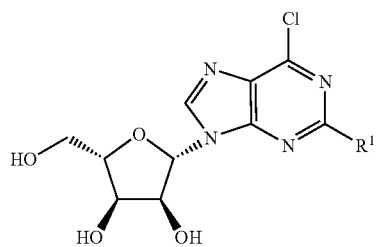

6

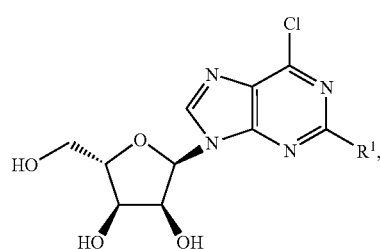

7 wherein R¹ is as defined above for the Purine Derviatives of Formula (I).

The compound of Formula 1 can be coupled with a compound of Formula 2 using lithium hexamethyldisilazide and trimethylsily triflate, followed by acetonide removal using trifluoroacetic acid to provide 6-chloroadenosine intermediates of Formula 3 and their corresponding other anomers of Formula 4. Similarly, the compound of Formula 5 can be coupled with a compound of Formula 2 using lithium hexamethyldisilazide and trimethylsilyl triflate, followed by acetonide removal using trifluoroacetic acid to provide compounds of Formula 6 and their corresponding other anomers of Formula 7.

Methodology useful for making the Purine Derivatives of Formula (I) is outlined in Scheme 2a.

Scheme 2a

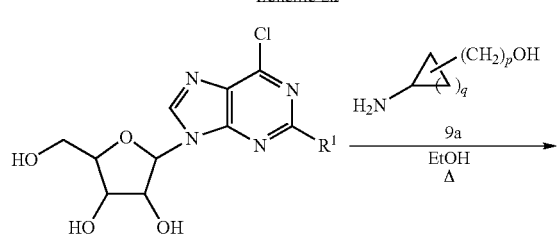

8a

-continued

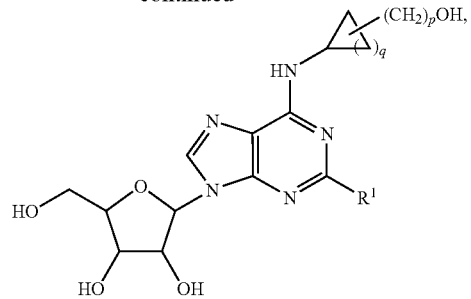

Purine Derivatives of Formula (I)

wherein R¹, p and q are as defined above for the Purine Derivatives of Formula (I).

A compound of formula 8a is reacted with a compound of formula 9a in refluxing ethanol to provide the Purine Derivatives of Formula (I).

Methodology useful for making the Purine Derivatives of Formula (I') is outlined in Scheme 2b.

Scheme 2b

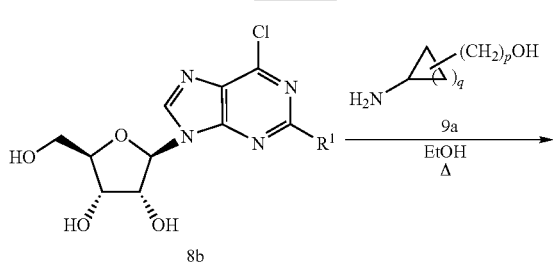

8b

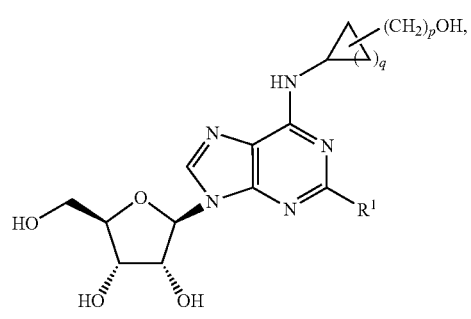

Purine Derivatives of Formula (I')

wherein R¹, p and q are as defined above for the Purine Derivatives of Formula (I').

A compound of formula 8b is reacted with a compound of formula 9a in refluxing ethanol to provide the Purine Derivatives of Formula (I'). A variety of compounds 9a, including particular stereoisomers, are commercially available from Acros Organics (Geel, Belgium), AFID Therapeutics Inc. (Lansing, Mich.), and Sigma-Aldrich (St. Louis, Mo.). In some embodiments, R¹ is —H or —Cl.

Scheme 3 sets forth methodology useful for making the compounds of formula 9, wherein p is 1 and q is defined above for the Purine Derivatives of Formula (I).

Scheme 3

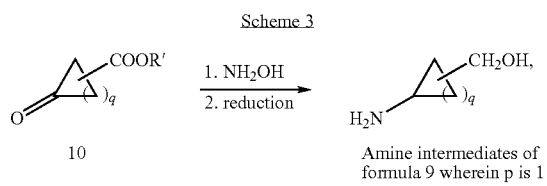

wherein R' is —H or methyl, p is 1 and q is defined above for the Purine Derivatives of Formula (I).

A compound of formula 10 is reacted with hydroxylamine in a solvent such as ethanol, and the resultant oxime is reduced, using for example, lithium aluminum hydride, to provide the compounds of formula 9, wherein p is 1 and q is 1, 2, 3, 4, 5 or 6.

The compounds of formula 10 are commercially available, or alternatively, can be prepared from commercially available starting materials using methods known to one skilled in the art of organic synthesis. For example, 1,2-substituted keto-esters of formula 10 can be synthesized by reacting a cycloalkanone enolate (prepared from a commercially available cycloalkanone) with an alkyl chloroform ate; 1,3-substituted keto-esters of formula 10 can be synthesized via 1,4 addition to a commercially available conjugated cycloalkenone; and 1,4-substituted keto-esters of formula 10 can be synthesized via oxidation of commercially available 4-carboxylate substituted cycloalkanols.

Scheme 4 sets forth methodology useful for making the compounds of formula 9, wherein p is an integer ranging from 3-6 and q is defined above for the Purine Deriviatives of Formula (I).

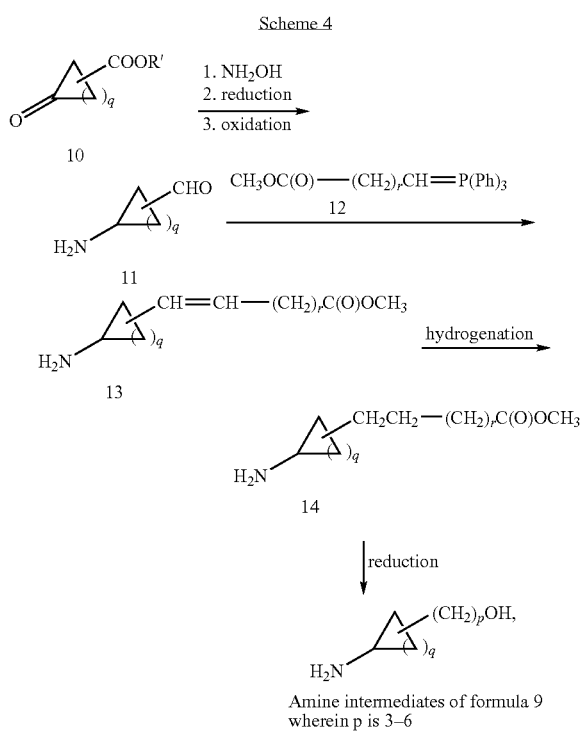

wherein R' is —H or methyl, p is an integer ranging from 3 to 6, q is defined above for the Purine Derivatives of Formula (I), and r is an integer ranging from 0 to 3.

A compound of formula 10 is reacted with hydroxylamine, and the resultant oxime is reduced, using for example, diisobutylaluminum hydride (DIBAL), to provide a compound of formula 11. The compound of formula 11 can be reacted with a compound of formula 12 via a Wittig reaction to provide a compound of formula 13 (See March, *Advanced Organic Chemistry: Reactions, Mechanisms, and Structure,* 956-963 (4$^{th}$ ed. 1992)). Hydrogenation of the compound of formula 13, using for example H$_2$ and Pd/C, provides the compound of formula 14, which can then be reduced using, for example, lithium aluminum hydride to provide the compounds of formula 9, wherein p is an integer ranging from 3-6 and q is defined above for the Purine Derivatives of Formula (I).

Scheme 5 sets forth methodology useful for making the amine intermediates of formula 9, wherein p is 2 and q is defined above for the Purine Deriviatives of Formula (I).

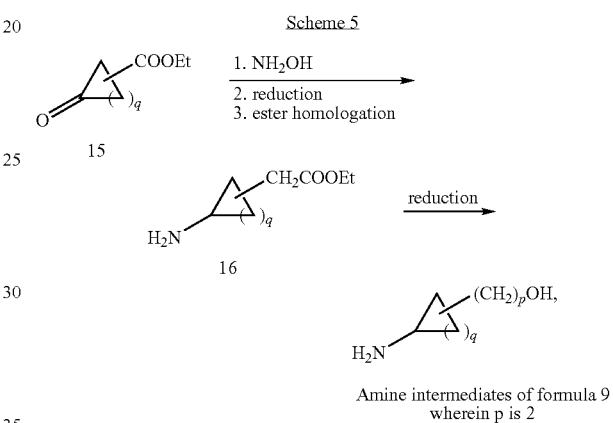

wherein p is an integer ranging from 3 to 6 and q is defined above for the Purine Derivatives of Formula (I).

A compound of formula 15 can be converted to the corresponding amine by reacting 15 with hydroxylamine followed by selective reduction of the resultant oxime using, for example, magnesium in the presence of ammonium formate (See Abiraj et al., *Synth. Commun.* 34:599-605 (2004)). A methylene group is then inserted between the the ethyl ester group and the carbocyclic ring of 15 using, for example, a Kowalski ester homologation reaction (Kowalski et al., *J. Am. Chem. Soc.* 57:7194 (1992)) to provide a compound of formula 16. The compound of formula 16 can then be reduced to the corresponding alcohol using, for example, lithium aluminum hydride to provide the compounds of formula 9, wherein p is 2 and q is defined above for the Purine Derivatives of Formula (I).

The compounds of formula 15 are commercially available, or alternatively, can be prepared from commercially available starting materials using methods known to one skilled in the art of organic synthesis.

4.4 Therapeutic/Prophylactic Administration and Compositions of the Invention Due to their activity, the Purine Derivatives are advantageously useful in veterinary and human medicine. As described above, the Purine Derivatives are useful for: (i) treating or preventing a Condition in an animal in need thereof; (ii) reducing an animal's core body temperature; or (iii) protecting an animal's heart against myocardial damage during cardioplegia.

When administered to an animal, the Purine Derivatives can be administered as a component of a composition that comprises a physiologically acceptable carrier or vehicle. The present compositions, which comprise a Purine Derivative, can be administered orally. The Purine Derivatives can also be administered by any other convenient route, for example, by infusion or bolus injection, by absorption through epithelial or mucocutaneous linings (e.g., oral, rectal, or intestinal mucosa) and can be administered together with another biologically active agent. Administration can be systemic or local. Various known delivery systems, including encapsulation in liposomes, microparticles, microcapsules, and capsules, can be used.

Methods of administration include, but are not limited to, intradermal, intramuscular, intraperitoneal, intravenous, subcutaneous, intranasal, intraocular, epidural, oral, sublingual, intracerebral, intravaginal, transdermal, rectal, by inhalation, or topical, particularly to the ears, nose, eyes, or skin. In some instances, administration will result in the release of the Purine Derivatives into the bloodstream. The mode of administration can be left to the discretion of the practitioner.

In one embodiment, the Purine Derivatives are administered orally.

In another embodiment, the Purine Derivatives are administered intravenously.

In another embodiment, when the Purine Derivatives are used to reduce an animal's core body temperature, the Purine Derviatives can be administered by continuous intravenous infusion.

In other embodiments, it can be desirable to administer the Purine Derivatives locally. This can be achieved, for example, and not by way of limitation, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In yet other embodiments, it can be desirable to administer the Purine Derivatives ocularly. Ocular administration of the Purine Derivatives can be achieved using an eye-dropper or a contact lens coated or impregnated with the Purine Derivative.

In certain embodiments, it can be desirable to introduce the Purine Derivatives into the central nervous system, circulatory system or gastrointestinal tract by any suitable route, including intraventricular, intrathecal injection, paraspinal injection, epidural injection, enema, and by injection adjacent to a peripheral nerve. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the Purine Derivatives can be formulated as a suppository, with traditional binders and carrier or vehicles such as triglycerides.

In another embodiment the Purine Derivatives can be delivered in a vesicle, in particular a liposome (see Langer, *Science* 249:1527-1533 (1990) and Lopez-Berestein et al., *Liposomes in the Therapy of Infectious Disease and Cancer* 317-327 and 353-365 (1989)).

In yet another embodiment the Purine Derivatives can be delivered in a controlled-release system or sustained-release system (see, e.g., Goodson, in Medical Applications of Controlled Release, supra, vol. 2, pp. 115-138 (1984)). Other controlled or sustained-release systems discussed in the review by Langer, *Science* 249:1527-1533 (1990) can be used. In one embodiment a pump can be used (Langer, *Science* 249:1527-1533 (1990); Sefton, *CRC Crit. Ref. Biomed. Eng.* 14:201 (1987); Buchwald et al., *Surgery* 88:507 (1980); and Saudek et al., *N. Engl. J Med.* 321:574 (1989)). In another embodiment polymeric materials can be used (see *Medical Applications of Controlled Release* (Langer and Wise eds., 1974); *Controlled Drug Bioavailability, Drug Product Design and Performance* (Smolen and Ball eds., 1984); Ranger and Peppas, *J. Macromol. Sci. Rev. Macromol. Chem.* 2:61 (1983); Levy et al., *Science* 228:190 (1935); During et al, *Ann. Neural.* 25:351 (1989); and Howard et al., *J. Neurosurg.* 71:105 (1989)).

In yet another embodiment a controlled- or sustained-release system can be placed in proximity of a target of the Purine Derivatives, e.g., the spinal column, brain, colon, skin, heart, lung, eye, or gastrointestinal tract, thus requiring only a fraction of the systemic dose.

The present compositions can optionally comprise a suitable amount of a physiologically acceptable carrier or vehicle.

Such physiologically acceptable carriers or vehicles can be liquids, such as water and oils, including those of petroleum, animal, vegetable, or synthetic origin, such as peanut oil, soybean oil, mineral oil, sesame oil and the like. The physiologically acceptable carriers or vehicles can be saline, gum acacia, gelatin, starch paste, talc, keratin, colloidal silica, urea and the like. In addition, auxiliary, stabilizing, thickening, lubricating, and coloring agents can be used. In one embodiment the physiologically acceptable carriers or vehicles are sterile when administered to an animal. Water can be a particularly useful when the Purine Derivative is administered intravenously. Saline solutions and aqueous dextrose and glycerol solutions can also be employed as liquid carriers or vehicles, particularly for injectable solutions. Suitable physiologically acceptable carriers or vehicles also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment the composition is in the form of a capsule. Other examples of suitable physiologically acceptable carrier or vehicles are described in *Remington's Pharmaceutical Sciences* 1447-1676 (Alfonso R. Gennaro eds., 19th ed. 1995), incorporated herein by reference.

In one embodiment the Purine Derivatives are formulated in accordance with routine procedures as a composition adapted for oral administration to human beings. Compositions for oral delivery can be in the form of tablets, lozenges, aqueous or oily suspensions, granules, powders, emulsions, capsules, syrups, or elixirs for example. Orally administered compositions can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active platform driving a Purine Derivative are also suitable for orally administered compositions. In these latter platforms, fluid from the environment surrounding the capsule can be imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard carriers or vehicles such as mannitol, lactose, starch, magnesium stearate, sodium saccharin, cellulose, and magnesium carbonate. In one embodiment the carriers or vehicles are of pharmaceutical grade.

In another embodiment the Purine Derivatives can be formulated for intravenous administration. Typically, compositions for intravenous administration comprise sterile isotonic aqueous buffer. Where necessary, the compositions can also include a solubilizing agent. Compositions for intravenous administration can optionally include a local anesthetic such as lignocaine to lessen pain at the site of the injection. The compositions' components can be supplied either separately or mixed together in unit dosage form, for example, as a dry lyophilized powder or water-free concentrate in a hermetically sealed container such as an ampule or sachette indicating the quantity of Purine Derivative. Where the Purine Derivatives are to be administered by infusion, they can be dispensed, for example, with an infusion bottle containing sterile pharmaceutical grade water or saline. Where the Purine Derivatives are administered by injection, an ampule of sterile water for injection or saline can be provided so that the ingredients can be mixed prior to administration.

The Purine Derivatives can be administered by controlled-release or sustained-release means or by delivery devices that are well known to those skilled in the art. Such dosage forms can be used to provide controlled- or sustained-release of one or more active ingredients using, for example, hydroxypropylmethyl cellulose, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those skilled in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled- or sustained-release.

In one embodiment a controlled- or sustained-release composition comprises a minimal amount of a Purine Derivative to treat or prevent the Condition, reduce an animal's core body temperature or protect an animal's heart against myocardial damage during cardioplegia in a minimal amount of time. Advantages of controlled- or sustained-release compositions include extended activity of the drug, reduced dosage frequency, and increased patient compliance. In addition, controlled- or sustained-release compositions can favorably affect the time of onset of action or other characteristics, such as blood levels of the Purine Derivative, and can thus reduce the occurrence of adverse side effects.

Controlled- or sustained-release compositions can initially release an amount of a Purine Derivative that promptly produces the desired therapeutic or prophylactic effect, and gradually and continually release other amounts of the Purine Derivative to maintain this level of therapeutic or prophylactic effect over an extended period of time. To maintain a constant level of the Purine Derivative in the body, the Purine Derivative can be released from the dosage form at a rate that will replace the amount of Purine Derivative being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

The amount of the Purine Derivative that is effective for treating or preventing a Condition, reducing an animal's core body temperature, or protecting an animal's heart against myocardial damage during cardioplegia, can be determined by standard clinical techniques. In addition, in vitro or in vivo assays can optionally be employed to help identify optimal dosage ranges. The precise dose to be employed can also depend on the route of administration, and the seriousness of the condition being treated and can be decided according to the judgment of a health-care practitioner. Suitable effective dosage amounts, however, range from about 10 micrograms to about 5 grams about every 4 h, although they are typically about 500 mg or less per every 4 hours. In one embodiment the effective dosage is about 0.01 mg, 0.5 mg, about 1 mg, about 50 mg, about 100 mg, about 200 mg, about 300 mg, about 400 mg, about 500 mg, about 600 mg, about 700 mg, about 800 mg, about 900 mg, about 1 g, about 1.2 g, about 1.4 g, about 1.6 g, about 1.8 g, about 2.0 g, about 2.2 g, about 2.4 g, about 2.6 g, about 2.8 g, about 3.0 g, about 3.2 g, about 3.4 g, about 3.6 g, about 3.8 g, about 4.0 g, about 4.2 g, about 4.4 g, about 4.6 g, about 4.8 g, and about 5.0 g, every 4 hours. Equivalent dosages can be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The number and frequency of dosages corresponding to a completed course of therapy can be determined according to the judgment of a health-care practitioner. The effective dosage amounts described herein refer to total amounts administered; that is, if more than one Purine Derivative is administered, the effective dosage amounts correspond to the total amount administered.

The amount of a Purine Derivative that is effective for treating or preventing a Condition, or protecting an animal's heart against myocardial damage during cardioplegia typically range from about 0.01 mg/kg to about 100 mg/kg of body weight per day, in one embodiment, from about 0.1 mg/kg to about 50 mg/kg body weight per day, and in another embodiment, from about 1 mg/kg to about 20 mg/kg of body weight per day.

The amount of a Purine Derivative that is effective for reducing an animal's core body temperature typically range from about about 1 µg/kg to about 10 mg/kg, in one embodiment, from about 0.1 mg/kg to about 5 mg/kg body weight per day, and in another embodiment, from about 1 mg/kg to about 2.5 mg/kg of body weight per day.

When a Purine Derviative is a component of a solution that is useful for maintaining the viability of an organ ex vivo, the concentration of the Purine Derivative in the solution that is effective for maintaining the viability of the organ is between about 1 nM to about 1 mM.

The Purine Derivatives can be assayed in vitro or in vivo for the desired therapeutic or prophylactic activity prior to use in humans. Animal model systems can be used to demonstrate safety and efficacy.

The present methods for treating or preventing a Condition, reducing an animal's core body temperature, or protecting an animal's heart against myocardial damage during cardioplegia, can further comprise administering another therapeutic agent to the animal being administered a Purine Derivative. In one embodiment the other therapeutic agent is administered in an effective amount.

Effective amounts of the other therapeutic agents are well known to those skilled in the art. However, it is well within the skilled artisan's purview to determine the other therapeutic agent's optimal effective amount range. In one embodiment of the invention, where, another therapeutic agent is administered to an animal, the effective amount of the Purine Derivative is less than its effective amount would be where the other therapeutic agent is not administered. In this case, without being bound by theory, it is believed that the Purine Derivatives and the other therapeutic agent act synergistically.

In one embodiment the other therapeutic agent is an anti-inflammatory agent. Examples of useful anti-inflammatory agents include, but are not limited to, adrenocorticosteroids, such as cortisol, cortisone, fluorocortisone, prednisone, prednisolone, 6α-methylprednisolone, triamcinolone, betamethasone, and dexamethasone; and non-steroidal anti-inflammatory agents (NSAIDs), such as aspirin, acetaminophen, indomethacin, sulindac, tolmetin, diclofenac, ketorolac, ibuprofen, naproxen, flurbiprofen, ketoprofen, fenoprofen, oxaprozin, mefenamic acid, meclofenamic acid, piroxicam, meloxicam, nabumetone, rofecoxib, celecoxib, etodolac, and nimesulide.

In another embodiment the other therapeutic agent is an anti-diabetic agent. Examples of useful anti-diabetic agents include, but are not limited to, glucagons; somatostatin; diazoxide; sulfonylureas, such as tolbutamide, acetohexamide, tolazamide, chloropropamide, glybenclamide, glipizide, gliclazide, and glimepiride; insulin secretagogues, such as repaglinide, and nateglinide; biguanides, such as metformin and phenformin; thiazolidinediones, such as pioglitazone, rosiglitazone, and troglitazone; and α-glucosidase inhibitors, such as acarbose and miglitol.

In another embodiment, the other therapeutic agent is an anti-glaucoma agent. Examples of anti-glaucoma agents include, but are not limited to, apraclonidine HCl, brimonidine tartrate, dipivefrin HCl, epinephrine HCl, betaxolol HCl, carteolol HCl, levobunolol HCl, metipranolol HCl, timolol, timolol maleate, pilocarpine HCl, pilocarpine, dorzolamide HCl, brinzolamide and latanoprost.

In a further embodiment the other therapeutic agent is an anti-cardiovascular-disease agent. Examples of useful anti-cardiovascular-disease agents include, but are not limited to, carnitine; thiamine; lidocaine; amiodarone; procainamide; mexiletine; bretylium tosylate; propanolol; sotalol; and muscarinic receptor antagonists, such as atropine, scopolamine, homatropine, tropicamide, pirenzipine, ipratropium, tiotropium, and tolterodine.

In another embodiment the other therapeutic agent is an analgesic agent. Examples of useful analgesic agents include, but are not limited to, buprenorphine, meperidine, morphine, codeine, propoyxphene, fentanyl, sufentanil, etorphine hydrochloride, hydrocodone, hydromorphone, nalbuphine, butorphanol, oxycodone, aspirin, ibuprofen, naproxen sodium, acetaminophen, xylazine, metedomidine, carprofen, naprosin, and pentazocine.

In a specific embodiment, the other therapeutic agent is buprenorphine.

In another embodiment, the other therapeutic agent is an antiemetic agent. Examples of useful antiemetic agents include, but are not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, or mixtures thereof.

A Purine Derivative and the other therapeutic agent can act additively or, in one embodiment, synergistically. In one embodiment, a Purine Derivative is administered concurrently with another therapeutic agent. In one embodiment, a composition comprising an effective amount of a Purine Derivative and an effective amount of another therapeutic agent can be administered. Alternatively, a composition comprising an effective amount of a Purine Derivative and a different composition comprising an effective amount of another therapeutic agent can be concurrently administered. In another embodiment, an effective amount of a Purine Derivative is administered prior or subsequent to administration of an effective amount of another therapeutic agent. In this embodiment, the Purine Derivative is administered while the other therapeutic agent exerts its therapeutic effect, or the other therapeutic agent is administered while the Purine Derivative exerts its preventative or therapeutic effect for treating or preventing a Condition, reducing an animal's core body temperature or protecting an animal's heart against myocardial damage during cardioplegia.

A composition of the invention can be prepared using a method comprising admixing a Purine Derivative and a physiologically acceptable carrier or vehicle. Admixing can be accomplished using methods well known for admixing a compound (or salt) and a physiologically acceptable carrier or vehicle.

4.6 Therapeutic or Prophylactic Uses of the Purine Derivatives

4.6.1 Treatment or Prevention of a Cardiovascular Disease

A cardiovascular disease can be treated or prevented by administration of an effective amount of a Purine Derivative.

Cardiovascular diseases that can be treated or prevented by administering an effective amount of a Purine Derivative include, but are not limited to, atherosclerosis, congestive heart failure, circulatory shock, cardiomyopathy, cardiac transplant, cardioplegia, and a cardiac arrhythmia.

In one embodiment, the cardiovascular disease is a cardiac arrhythmia, congestive heart failure, circulatory shock or cardiomyopathy.

In one embodiment, the cardiac arrhythmia is a tachycardia or an an idiotopic arrhythmia.

In still another embodiment, the tachycardia is atrial fibrillation, supraventricular tachycardia, atrial flutter, paroxysmal supraventricular tachycardia, paroxysmal atrial tachycardia, sinus tachycardia, atrioventricular nodal reentry tachycardia, or tachycardia caused by Wolff-Parkinson-White Syndrome.

In a further embodiment, the methods for treating a tachycardia include lowering the animal's cardiac ventricular rate to a rate of not less than about 40 beats per minute. In one embodiment, the methods are useful for lowering an animal's cardiac ventricular rate to a rate of from about 60 beats per minute to about 100 beats per minute. In another embodiment, the methods are useful for lowering an animal's cardiac ventricular rate to a rate of from about 100 beats per minute to about 140 beats per minute.

In another embodiment, the Purine Derivatives are useful for converting a cardiac arrhythmia to a normal sinus rhythm. Accordingly, the invention encompasses methods for converting a cardiac arrhythmia to a normal sinus rhythm, comprising administering an effective amount of a Purine Derivative to an animal in need thereof.

4.6.2 Protecting an Animal's Heart Against Myocardial Damage During Cardioplegia In one embodiment, the invention provides methods for inducing cardioplegia comprising administering to an animal in need thereof an effective amount of a cardioplegia-inducing agent and a Purine Derivative. Cardioplegia-inducing agents useful in the present invention include, but are not limited to, potassium chloride, procaine, lidocaine, novocaine, bupivocaine, nicorandil, pinacidil, halothane, St. Thomas solution, Fremes solution, 2,3-butanedione monoxime, and esmolol.

In one embodiment, the cardioplegia-inducing agent is lidocaine.

In one embodiment, a cardioplegia-inducing agent and a Purine Derivative are present within the same composition. The present methods for inducing cardioplegia are useful for preventing or minimizing myocardial damage from occurring during cardioplegia.

In yet another embodiment, the invention provides methods for protecting an animal's heart against myocardial damage during cardioplegia, the method comprising administering to an animal in need thereof an effective amount of a Purine Derivative.

In still another embodiment, the invention provides methods for inducing cardioplegia in an animal while protecting an animal's heart against myocardial damage during the cardioplegia, the method comprising administering to an animal in need thereof an effective amount of:

(a) a cardioplegia-inducing agent; and
(b) a Purine Derivative.

In one embodiment, the cardioplegia-inducing agent is administered prior to the administration of the Purine Derivative.

In another embodiment, Purine Derivative is administered prior to the administration of the cardioplegia-inducing agent.

In a further embodiment, the cardioplegia-inducing agent and the Purine Derivative are administered concurrently.

In another embodiment, the cardioplegia-inducing agent and the Purine Derivative are administered such that the Purine Derivative exerts its prophylactic effect of protection against myocardial damage while the cardioplegia-inducing agent exerts its cardioplegic effect.

4.6.3 Treatment or Prevention of a Neurological Disorder

A neurological disorder can be treated or prevented by administration of an effective amount of a Purine Derivative.

Neurological disorders that can be treated or prevented by administering an effective amount of a Purine Derivative include, but are not limited to, a seizure disorder, such as epilepsy; pain, including acute postoperative pain, cancer pain, neuropathic pain, pain resulting from surgery, labor pain during childbirth, a psychogenic pain syndrome, and headache, including migraine headache and cluster headache; delirium and dementia, such as Lewy body dementia, Alzheimer's disease, Pick's disease, or a Creutzfeldt-Jakob disease; a sleep disorder, such as insomnia, hypersomnia, a sleep apnea syndrome, restless-leg syndrome, or a parasomnia; a cranial nerve disorder, such as Bell's palsy; a disorder of movement, such as tremor, dystonia, Tourette's Syndrome, myoclonus, Huntington's disease, cortico basal degeneration, chorea, a drug-induced movement disorder, progressive supranuclear palsy, Parkinson's disease, or a Parkinsonian Syndrome, such as multiple system atrophy, Wilson's disease or mult-infarct state; a demyelinating disease, such as multiple sclerosis or amyotrophic lateral sclerosis; a neuro-muscular disease, such as muscular dystrophy; a cerebrovascular disease, such as stroke; a neuroopthalmic disorder; a psychiatric disorder, including but not limited to, a somatoform disorder, such as hypochondriasis or body dysmorphic disorder; a dissociation disorder, such as panic disorder, a phobic disorder, or an obsessive-compulsive disorder; a mood disorder, such as depression or a bipolar disorder; a personality disorder; a psychosexual disorder; suicidal behavior; schizophrenia; brief psychotic disorder; and delusional disorder.

In one embodiment, the neurological disorder treated or prevented is epilepsy, pain, or stroke.

In one embodiment, the present methods for treating pain further comprise the administration of an additional analgesic agent. In a specific embodiment, the additional analgesic agent is buprenorphine.

4.6.4 Treatment or Prevention of an Ophthalmic Condition

An ophthalmic condition can be treated or prevented by administration of an effective amount of a Purine Derivative.

Ophthalmic conditions that can be treated or prevented by administering an effective amount of a Purine Derivative include, but are not limited to, glaucoma with normal intraocular pressure, glaucoma with intraocular hypertension, pseudoexfoliation syndrome, ischemic retinopathy, diabetic retinopathy, and acute macular degeneration.

In one embodiment, the neurological disorder treated or prevented is glaucoma with intraocular hypertension or glaucoma with normal intraocular pressure.

4.6.5 Treatment or Prevention of an Ischemic Condition

An ischemic condition can be treated or prevented by administration of an effective amount of a Purine Derivative.

Ischemic conditions that can be treated or prevented by administering an effective amount of a Purine Derivative include, but are not limited to, stable angina, unstable angina, myocardial ischemia, hepatic ischemia, mesenteric artery ischemia, intestinal ischemia, myocardial infarction, critical limb ischemia, chronic critical limb ischemia, cerebral ischemia, acute cardiac ischemia, and an ischemic disease of the central nervous system, such as stroke or cerebral ischemia.

In one embodiment, the ischemic condition is myocardial ischemia, stable angina, unstable angina, stroke, ischemic heart disease or cerebral ischemia.

4.6.6 Treatment or Prevention of a Reperfusion Injury

A reperfusion injury can be treated or prevented by administration of an effective amount of a Purine Derivative. Reperfusion injury can result following a naturally occurring episode, such as a myocardial infarction or stroke, or during a surgical procedure where blood flow in vessels is intentionally or unintentionally blocked.

Reperfusion injuries that can be treated or prevented by administering an effective amount of a Purine Derivative include, but are not limited to, intestinal reperfusion injury, myocardial reperfusion injury; and reperfusion injury resulting from cardiopulmonary bypass surgery, thoracoabdominal aneurysm repair surgery, carotid endaretectomy surgery, or hemorrhagic shock.

In one embodiment, the reperfusion injury results from cardiopulmonary bypass surgery, thoracoabdominal aneurysm repair surgery, carotid endaretectomy surgery or hemorrhagic shock.

4.6.7 Treatment or Prevention of Diabetes

Diabetes can be treated or prevented by administration of an effective amount of a Purine Derivative.

Types of diabetes that can be treated or prevented by administering an effective amount of a Purine Derivative include, but are not limited to, Type I diabetes (Insulin Dependent Diabetes Mellitus), Type II diabetes (Non-Insulin Dependent Diabetes Mellitus), gestational diabetes, insulinopathy, diabetes due to pancreatic disease, diabetes associated with another endocrine disease (such as Cushing's Syndrome, acromegaly, pheochromocytoma, glucagonoma, primary aldosteronism or somatostatinoma), Type A insulin resistance syndrome, Type B insulin resistance syndrome, lipatrophic diabetes, and diabetes induced by β-cell toxins.

In one embodiment, the diabetes is Type I diabetes mellitus.

In another embodiment, the diabetes is Type II diabetes mellitus.

4.6.8 Methods for Reducing an Animal's Core Body Temperature

In one embodiment, the invention provides methods for reducing an animal's core body temperature, comprising administering to an animal in need thereof an effective amount of a Purine Derivative.

Reducing an animal's core body temperature is useful for slowing metabolism or reducing oxygen consumption, particularly where oxygen delivery to a tissue is inadequate. Examples of conditions characterized by inadequate oxygen delivery to a tissue include, but are not limited to: (i) a medical procedure, such as heart surgery, brain surgery, organ transplantation, mechanical occlusion of the vascular supply, or vascular stenosis; (ii) a disorder or medical condition such as ischemia, a respiratory disorder, respiratory failure, a pulmonary disorder, anemia, anaphylactic shock, hemmorhagic shock, dehydration, compartment syndrome, intravascular thrombus, septic shock, cystic fibrosis, lung cancer, stroke, a burn, or internal bleeding; (iii) an injury such as drowning, a crush injury to one or more limbs, choking, or suffocation; (iv) a compromised airway due to asthma, a tumor, a lung injury or a tracheal injury; (v) an external compression of one or more blood vessels; or (vi) an intrinsic obstruction of one or more blood vessels.

Accordingly, the present invention encompasses methods for slowing an animal's heart rate during heart surgery; protecting an animal's tissue from damage during surgery, particular heart or brain surgery; reducing intracranial hypertension caused by brain injury in an animal; or inducing hibernation in an animal, each method comprising administering an effective amount of a Purine Derivative to an animal in need thereof.

Reducing an animal's core body temperature is also useful for reducing an animal's rate of oxygen consumption. Accordingly, the present invention provides methods for reducing the rate of an animal's oxygen consumption, the method comprising administering to an animal in need thereof an effective amount of a Purine Derivative.

Reducing an animal's core body temperature is useful for treating or preventing tissue damage or stroke, resulting from an inadequate supply of oxygen to a cell, a tissue, an organ or an organ system.

In one embodiment, an animal's core body temperature is reduced to increase emergency recussitation in an injured animal.

In another embodiment, an animal's core body temperature is reduced prior to and/or during heart surgery. In a specific embodiment, the animal is a human child undergoing pediatric heart surgery.

In another embodiment, an animal's core body temperature is reduced to treat respiratory failure in an animal.

In one embodiment, an animal's core body temperature is reduced to aid tissue metabolism in an animal whose respiration and ventilation is facilitated by a ventilator. In a specific embodiment, the animal whose respiration and ventilation is facilitated by a ventilator is a geriatric human. In another specific embodiment, the animal whose respiration and ventilation is facilitated by a ventilator is a premature human infant.

In one embodiment, an organ can be stored ex vivo in a composition comprising an effective amount of a Purine Derivative. The composition is useful for preserving an organ's viability after being removed from a donor and before the organ is transplanted in a recipient. In one embodiment, the donor and recipient are the same.

In another embodiment, an effective amount of a Purine Derivative can be administered to an animal awaiting organ transplantation to reduce the animal's core body temperature prior to or during organ transplantation.

In one embodiment, the animal's core body temperature is reduced to a temperature of from about 4° C. to about 34° C. In certain embodiments, the animal's core body temperature is reduced to about 34° C., to about 30° C., to about 25° C., to about 20° C., to about 15° C., to about 10° C., or to about 4° C.

In a specific embodiment, an animal's core body temperature is reduced to induce therapeutic hypothermia.

4.6.9 Treatment or Prevention of Obesity

Obesity can be treated or prevented by administration of an effective amount of a Purine Derivative.

Types of obesity that can be treated or prevented by administering an effective amount of a Purine Derivative include, but are not limited to, android obesity, gynoid obesity, abdominal obesity, age-related obesity, diet-induced obesity, fat-induced obesity, hypothalamic obesity, morbid obesity, multigenic obesity, and visceral obesity.

In one embodiment, the obesity is android obesity.

4.6.10 Treatment or Prevention of a Wasting Disease

In one embodiment, the invention provides methods for treating or preventing a wasting disease, comprising administering to an animal in need thereof an effective amount of a Purine Derivative.

Types of wasting diseases that can be treated or prevented by administering an effective amount of a Purine Derivative include, but are not limited to, chronic wasting disease, cancer wasting syndrome, and AIDS wasting syndrome.

The following examples are set forth to assist in understanding the invention and should not, of course, be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

5. EXAMPLES

Materials: [³H]NECA was obtained from Du Pont NEN, Dreieich, Germany. Other unlabeled adenosine receptor agonists and antogonists can be obtained from RBI, Natick, Mass. The 96-well microplate filtration system (MultiScreen MAFC) was obtained from Millipore, Eschborn, Germany. Penicillin (100 U/mL), streptomycin (100 μg/mL), L-glutamine and G-418 were obtained from Gibco-Life Technologies, Eggenstein, Germany. Other materials can be obtained as described in Klotz et al., *J. Biol. Chem.*, 260:14659-14664, 1985; Lohse et al., *Naunyn-Schmiedeberg's Arch. Pharmacol.*, 336:204-210, 1987; and Klotz et al., *Naunyn-Schmiedeberg's Arch. Pharmacol.*, 357:1-9, 1998.

General Methods: Proton nuclear magnetic resonance (NMR) spectra were obtained from Varian 300 MHz spectrophotometer and chemical shifts are reported in parts per million. Compounds were characterized on the basis of NMR and Mass spectral (MS) data. 6-Chloroadenosine was purchased from TRC, Ontario, Canada. 2,6-dichloroadenosine was purchased from ACROS Organic, USA.

5.1 Example 1

Preparation of Compound I'-1

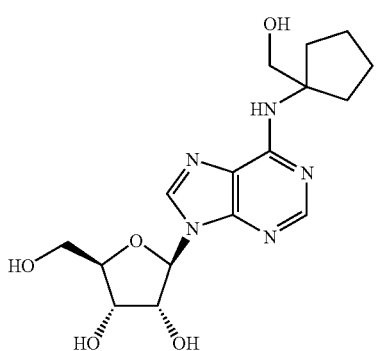

6-Chloroadenosine (Aldrich, 1.145 g, 4 mmol) was diluted with ethanol (50 mL) and to the resultant solution was added 1-hydroxymethylcyclopentylamine (1.0 g, 8 mmol). The resultant reaction mixture was heated to reflux and allowed to stir at reflux for about 15 hours. The resultant reaction mixture was cooled to room temperature, then concentrated in vacuo to provide a crude residue. The crude residue was purified using flash column chromatography (silica gel column using 8% methanol-dichloromethane as eluent) to provide Compound I'-1 (0.383 gm). ¹H NMR (DMSO-d₆): δ 1.51-1.62 (m, 2H), 1.7-1.82 (m, 4H), 2.10-2.18 (m, 2H), 3.16 (d, J=5.1 Hz, 1H), 3.50-3.58 (m, 1H), 3.62-3.68 (m, 2H), 3.95 (bs, 1H), 4.09-4.15 (m, 1H), 4.58-4.66 (m, 1H), 5.06-5.10 (m, 1H), 5.18 (d, J=4.2 Hz, 1H), 5.35-5.40 (m, 1H), 5.44 (d, J=6 Hz, 1H), 5.87 (d, J=6 Hz, 1H), 6.85 (s, 1H), 8.20 (s, 1H), 8.36 (s, 1H); MS (ES⁺): m/z 366 (M+1).

5.2 Example 2

Preparation of Compound I'-19

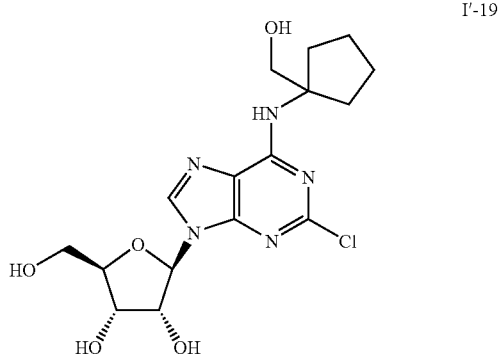

2,6-Dichloroadenosine (Aldrich, 0.4 gm, 0.0012 mol) was diluted with ethanol (25 ml) and to the resultant solution was added I-hydroxymethylcyclopentylamine (1 gm, 0.008 mol). The resultant reaction mixture was heated to reflux and allowed to stir at reflux for about 6 hours. The resultant reaction mixture was then cooled to room temperature and concentrated in vacuo. The resultant residue was purified using flash column chromatography (silica gel column using 8% methanol-dichloromethane eluent) to provide Compound I'-19 (365 mg, 83%). ¹H NMR (DMSO-d₆): δ 1.51-1.62 (m, 2H), 1.71-1.82 (m, 4H), 2.10-2.18 (m, 2H), 3.50 (m, 1H), 3.62-3.65 (m, 2H), 3.94 (bs, 1H), 4.12 (bs, 1H), 4.51 (d, J=5.4 Hz, 1H), 4.97 (bs, 1H), 5.07-5.09 (m, 1H), 5.22-5.24 (m, 1H), 5.48-5.50 (m, 1H), 5.77 (d, J=2.4 Hz, 1H), 5.80 (m, 1H), 7.42 (s, 1H), 8.40 (s, 1H); MS (ES⁺): m/z 400 (M+1).

5.3 Example 3

Preparation of Compounds I'-7, I'-91a, I'-92a, I'-92b, I'-93a, I'-94a, I'-95a, and I'-95b Compounds I'-7, I'-91a, I'-92a, I'-92b, I'-93a, I'-94a, I'-95a, and I'-95b were prepared according to the general methodology described in Examples 1 and 2 and elsewhere herein. These compounds were characterized by mass spectroscopy as set forth in Table 1 below.

TABLE 1

| Mass spectroscopic characterization for illustrative Purine Derivatives | |
|---|---|
| Compound | MS (ES⁺): m/z [M + 1] |
| I'-7 | 366.4 |
| I'-91a | 366.4 |
| I'-92a | 380.3 |
| I'-92b | 380.3 |
| I'-93a | 380.3 |
| I'-94a | 400.4 |
| I'-95a | 414.4 |
| I'-95b | 414.4 |

5.4 Example 4

Cell Culture and Membrane Preparation For Adenosine Receptor Binding Studies CHO cells stably transfected with human adenosine $A_1$ receptor were grown and maintained in Dulbecco's Modified Eagles Medium with nutrient mixture F12 (DMEM/F12) without nucleosides, containing 10% fetal calf serum, penicillin (100 U/mL), streptomycin (100 µg/mL), L-glutamine (2 mM) and Geneticin (G-418, 0.2 mg/mL; $A_{2B}$, 0.5 mg/mL) at 37° C. in 5% $CO_2$/95% air. Cells were then split 2 or 3 times weekly at a ratio of between 1:5 and 1:20.

Membranes for radioligand binding experiments were prepared from fresh or frozen cells as described in Klotz et al., *Naunyn-Schmiedeberg's Arch. Pharmacol.*, 357:1-9 (1998). The cell suspension was then homogenized in ice-cold hypotonic buffer (5 mM Tris/HCl, 2 mM EDTA, pH 7.4) and the resultant homogenate was spun for 10 minutes (4° C.) at 1,000 g. The membranes were then sedimented from the supernatant for 30 minutes at 100,000 g and resuspended in 50 mM Tris/HCl buffer pH 7.4 (for $A_3$ adenosine receptors: 50 mM Tris/HCl, 10 mM $MgCl_2$, 1 mM EDTA, pH 8.25), frozen in liquid nitrogen at a protein concentration of 1-3 mg/mL and stored at −80° C.

5.5 Example 5

Adenosine Receptor Binding Studies

The affinities of selected Purine Derivatives for the adenosine $A_1$ receptor were determined by measuring the displacement of specific [$^3$H]2-chloro-$N^6$-cyclopentyl adenosine (Perkin-Elmer Life Sciences) binding in CHO cells stably transfected with human recombinant $A_1$ adenosine receptor expressed as Ki (nM).

Dissociation constants of unlabeled compounds ($K_i$-values) were determined in competition experiments in 96-well microplates using the $A_1$ selective agonist 2-chloro-$N^6$-[$^3$H] cyclopentyladenosine ([$^3$H]CCPA, 1 nM) for the characterization of $A_1$ receptor binding. Nonspecific binding was determined in the presence of 100 µM R-PIA and 1 mM theophylline, respectively. For details see Klotz et al., *Naunyn-Schmiedeberg's Arch. Pharmacol.*, 357:1-9, 1998. All binding data were calculated by non-linear curve fitting using the program SCTFIT (De Lean et al., *Mol. Pharm.* 1982, 21:5-16).

Results are presented in Table 2 below.

TABLE 2

Affinities of illustrative Purine Derivatives for human $A_1$, $A_{2A}$ and $A_3$ adenosine receptors

| Compound | Ki($A_1$)[a] (nM) | Ki($A_{2A}$)[b] (nM) | Ki($A_3$)[c] (nM) |
|---|---|---|---|
| [$^3$H]CCPA | 0.83 (0.55-1.25) | 2,270 (1,950-2,660) | 42.3 (32.1-55.8) |
| I'-1 | 6.77 (6.00-7.63) | 28,100 (21,200-37,300) | 7,700 (5,480-10,800) |
| I'-19 | 6.47 (5.91-7.09) | 24,000 (17,600-32,800) | 5,960 (4,140-8,600) |

[a]Displacement of specific [$^3$H]CCPA binding in CHO cells stably transfected with human recombinant $A_1$ adenosine receptor, expressed as Ki (nM).
[b]Displacement of specific [$^3$H]NECA binding in CHO cells stably transfected with human recombinant $A_{2A}$ adenosine receptor, expressed as Ki (nM).
[c]Displacement of specific [$^3$H]NECA binding in HEK cells stably transfected with human recombinant $A_3$ adenosine receptor, expressed as Ki (nM).
All data are geometric means with 95% confidence intervals in parentheses.

The data set forth in Table 2 demonstrate that Compounds I'-1 and I'-9, illustrative Purine Derivatives, selectively bind the adenosine $A_1$ receptor and accordingly, are useful for treating or preventing a Condition, slowing an animal's metabolic rate, or protecting an animal's heart against myocardial damage during cardioplegia.

5.6 Example 6

Determination of the Effects of the Purine Derivatives on Septic Shock

Male BALB/c mice (6-8 weeks of age) are used in studies investigating lipopolysaccharide-induced cytokine production and survival. For cytokine production the mice are treated with an illustrative Purine Derivative (0.03 mg/kg) orally by gavage 30 minutes and are then subjected to lipopolysaccharide (1 mg/kg i.p.) for 90 minutes. After this period blood is taken and serum obtained for analysis. Serum is diluted 1:5 prior to being assayed for cytokines using species-specific ELISA kits (R & D Systems) for the chemokine MIP-1α and the cytokine TNF-α levels, which are expressed as pg/mL. For survival studies mice can be treated with an illustrative Purine Derivative (oral administration of 0.03 mg/kg) starting 30 minutes prior to the mice being subjected to lipopolysaccharide (55 mg/kg i.p.). The survival of the mice is determined and followed over 72 hours and expressed as a percentage of surviving mice at each time point.

5.7 Example 7

Determination of the Anti-Arrhythmia Effects of the Purine Derivatives

Heart Perfusion

Male Sprague-Dawley rats (having a body weight of 250 to 300 g) are heparinized using sodium heparin (1,000 U/kg i.p.), followed 10 minutes later by introduction of anesthesia via intraperitoneal administration of sodium pentobarbital (40 mg/kg). Once the animal is anesthetized, the thorax is opened, and the heart is rapidly removed and perfused through the ascending aorta using Krebs-Ringer buffer consisting of NaCl (118 mmol/liter), KCl (4.75 mmol/liter), $KH_2PO_4$ (1.18 mmol/liter), $MgSO_4$ (1.18 mmol/liter), $CaCl_2$ (2.5 mmol/liter), $NaHCO_3$ (25 mmol/liter), and glucose (11 mmol/liter). A mixture of 95% $O_2$ and 5% $CO_2$ at 37° C. is then bubbled through the perfusate (the heart is initially perfused at a constant pressure of 70 mm Hg). About 10 minutes after the constant pressure perfusion, perfusion is switched to constant flow perfusion achieved using a microtube pump. The perfusion pressure is maintained at the same level of constant pressure perfusion by adjusting flow rate. Once the flow rate is determined, it is maintained throughout the experiment. The hearts are stimulated by rectangular pulses at a rate of 5 Hz and 2-millisecond duration and twice the diastolic threshold, delivered from a stimulus isolation unit (ADInstruments Ltd, Australia).

Effect of the Purine Derivatives on Ischemia-Induced Arrhythmias

Rat hearts are perfused at constant pressure of 70 mmHg without pacing as described above. Bipolar epicardial electrocardiogram (ECG) is recorded by placing two electrodes on the surface of right appendage and apex. A stainless steel cannula is used as an indifferent electrode. The ECG and heart rate are continuously monitored and data are recorded using a PowerLab data acquisition system (ADInstruments Ltd, Australia) in conjunction with a computer, and analyzed using the Chart.3 computer package. After a 20-minute equilibration period, regional ischemia is induced by ligation of the left anterior descending (LAD) coronary artery, and the ligature is released 30 minutes after occlusion. An illustrative Purine Derivative is applied interperfusate 10 minutes before LAD ligation and is present during LAD ligation. An illustrative Purine Derivative is to be tested at 10, 30 and 100 pM concentrations.

5.8 Example 8

Determination of the Effect of the Purine Derivatives on Function Recovery After Global Ischemia/Reperfusion Effect of an Illustrative Purine Derivative on Function Recovery After Ischemia/Reperfusion Rat hearts are initially perfused at a constant pressure of 70 mm Hg using the procedure described above in Example 7. After a 20 minute stabilization period, hearts are subjected to 30 minute no-flow ischemia followed by 40 minute reperfusion. In treated hearts, an illustrative Purine Derivative is infused for 10 minutes prior to induction of ischemia. $+dp/dt_{max}$ is measured after 30 minutes of ischemia followed by 40 minutes of reperfusion to determine the effect on myocardial contractility (dp/dt).

5.9 Example 9

Determination of the Effect of the Purine Derivatives on Pain

Male mice (body weight of 25-35 grams) are put into groups as follows: a first group which is to be intreperitoneally administered buprenorphine (0.3 mg/kg), a second group which is to be intreperitoneally administered buprenorphine (1 mg/kg), a third group which is to be intreperitoneally administered an illustrative Purine Derivative (3 mg/kg), a fourth group which is to be intreperitoneally co-administered an illustrative Purine Derivative (3 mg/kg) and buprenorphine (1.0 mg/kg), and a fifth group which is to be intreperitoneally co-administered an illustrative Purine Derivative (3 mg/kg) and buprenorphine (0.3 mg/kg). The analgesic effects in mice are measured using an IITC model 33 tail-flick analgesia meter (IITC Inc., Woodland Hills, Calif.) at 0 minutes (baseline control), 5 minutes, 15 minutes, 30 minutes and 60 minutes (in some cases also 90 and 120 minutes) post-treatment, compound or vehicle treatment. The average recording value of two readings should be used for each time point. A baseline of between 2-4 seconds of latency for each mouse and a 10-second cut-off time is set for the maximum possible effect of analgesia (% MPE). % MPE is calculated using the following formula: % MPE=[(post-drug value−baseline)/(cut-off time−baseline)]×100.

5.10 Example 10

Determination of the Effect of the Purine Derivatives on Pain

Male mice (each having a body weight of 20-30 g) are subcutaneously administered 20 µl of a 1% formalin solution in formaldehyde (prepared by diluting a commercial 4% [w/v] stock formnalin solution) into the dorsal region of their left hind paw. The mice are then assigned to either a control group and administered vehicle, or to a treatment group. Each group is then intraperitoneally administered an illustrative Purine Derivative (1.0 mg/kg). Both groups of animals are then monitored for a reaction for 30 minutes post-treatment to determine how much time each animal spends licking the treated paw. The licking time in control group (vehicle pretreated animals) is then compared to the licking time in the treatment group in order to calculate the analgesic effect. The 30 minute reaction period is divided into two phases: an early phase which lasts from 0-5 minutes post-treatment, and a late phase which lasts from 10-30 minutes post-treatment.

5.11 Example 11

Determination of the Effect of the Purine Derivatives on Pain

BALB/C mice (6-8 weeks of age) are intraperitoneally administered streptozotocin (40 mg/kg, once per day for 5 consecutive days) to induce diabetes (blood glucose levels are greater than 200 mg/mL). Three weeks after the first streptozotocin injection, the animals are intraperitoneally administered an illustrative Purine Derivative (1 mg/kg) into a rear paw and post-treatment allodynia can be measured using an Electrovonfrey anesthesiometer (IITC Inc., Woodland Hills Calif. 91367). The analgesic activity of an illustrative Purine Derivative is measured at 0 minutes (control), 15 minutes, 30 minutes and 60 minutes time point after administration of an illustrative Purine Derivative.

5.12 Example 12

Determination of the Effect of the Purine Derivatives on Pain

Male Wistar rats (each weighing between 200-250 g, kept under pathogen-free conditions at 24-25° C. and provided with standard rat chow and water ad libitum) are anaesthetized via intraperitoneal administration of pentobarbital (50 mg/kg) and placed in a stereotaxic frame. The atlanto-occipital membrane is exposed and a PE-10 catheter (7.5 cm) is inserted through an incision into the subarachnoidal space. The external end of the catheter is then fixed to the skull, the wound is closed, and the rats are allowed to recover for 7 days post-surgery. Animals without neurological deficits are placed in a plexiglass observation chamber on a metal mesh surface and mechanical thresholds of the plantar surface of the paw can be determined using a Dynamic Plantar Aesthesiometer (Ugo Basile, Italy) as follows: Following acclimation, the touch stimulator unit is placed under the animal's paw such that the filament is positioned under the target area of the paw. The filament is then lifted such that it contacted the pad of the animal's paw and continually exerted an increasing upward force on the paw until the animal withdrew the paw. The paw withdrawal threshold is measured 5 times in this manner in turns and the mean of the 5 values is calculated. After control threshold measurements are complete, carrageenan (3%, 100 µl) is administered subcutaneously into a hindpaw, resulting in marked swelling and redness of the treated paw. Three hours after the carrageenan administration, the threshold values are measured again. The animals are then divided into a control group (administered vehicle intrathecally) and a treatment group (adminstered an illustrative Purine Derivative intrathecally at in a 10 µl injection volume). Threshold determinations are repeated as described above at 15 minutes, 30 minutes, 60 minutes, 90 minutes and 120 minutes after the administration of vehicle or an illustrative Purine Derivative.

5.13 Example 13

Determination of the Effect of the Purine Derivatives on Pain

Male CD rats (each weighing from 220 g to 250 g) are prepared according to the procedure set forth in Z. Seltzer et al., *Pain,* 43:205-218 (1990). The rats are then anesthetized via intraperitoneal administration of sodium pentobarbital (50 mg/kg). A skin incision is made at the upper ⅓ and ⅔ left thigh area of each rat and the left sciatic nerve is exposed and freed from the surrounding connective tissue. An 8-0 nylon suture is then used to tightly ligate the left sciatic nerve of each rat so that the dorsal ⅓ to ½ of the nerve thickness is trapped in the ligature. The incision is closed using 4-0 sterile suture. Seven days post-surgery, the animals are put into four groups: a first group that is administered vehicle (control group); a second group that is administered an illustrative Purine Derivative at 0.1 mg/kg; a third group that is administered buprenorphine at 0.3 mg/kg; and a fourth group that is co-administered an illustrative Purine Derivative at 0.1 mg/kg and buprenorphine at 0.3 mg/kg. Animals in all four groups are assessed for allodynia immediately prior to treatment and at 10, 20, 30 and 60 minutes post-treatment using the Von Frey Hair test (G. M. Pitcher et al., *J Neurosci Methods,* 87:185-93 (1999)).

5.14 Example 14

Determination of the Effect of the Purine Derivatives on Heart Rate

Adult male Wistar rats (each weighing from about 350 g to about 400 g) are anesthetized as in Example 12, then prepared for monitoring of blood pressure and heart rate. Each animal's heart rate is measured, then an illustrative Purine Derivative is intravenously administered via the femoral vein at a dose of 1 ng/kg/minute, 10 ng/kg/minute, or 1000 ng/kg/minute (n=2 animals per dosage size) for a total administration period of 20 minutes. Each animal's heart rate is then remeasured. The post-treatment heart rate is then compared to the pre-treatment heart rate.

5.15 Example 15

Determination of the Effect of the Purine Derivatives on Core Body Temperature

Two male Sprague-Dawley rats of about 400 g each were kept at 13° C. and slowly injected with 20 mg/mL of Compound I'-1 dissolved in saline through a jugular venus (JV) catheter for about 2 minutes to reach a dose of 15 mg/kg. After the rats fell asleep, 20 mg/mL of Compound I'-1 was continuously injected through the jugular venus catheter via a syringe pump for 4 hours at a rate 1 mL/h. The rats were then returned to their cages at room temperature. Their rectal temperature, respiratory rate, and behavior were recorded following 5 min, 10 min, 20 min, 30 min, 1 h, 1.5 h, 2 h, 2.5 h, 3 h, 3.5 h, and 4 h. Both animals survived the experiment. The results are shown in Table 3A and Table 3B.

TABLE 3A

Parameters in the Determination of the Effect of the Purine Derivatives on Core Body Temperature Up to 30 Minutes

| Animal # | Parameters | Time | | | | |
|---|---|---|---|---|---|---|
| | | 0 min | 5 min | 10 min | 20 min | 30 min |
| 1 | Rectal Temperature | 38 | 38 | 37 | 36 | 36 |
| | Respiratory Rate (/min) | 210 | — | 69 | 66 | 75 |
| | Behavior | normal | sleep/move | sleep/move | sleep | sleep |
| 2 | Rectal Temperature | 39 | 39 | 38 | 37 | 37 |
| | Respiratory Rate (/min) | 220 | 99 | 84 | 57 | 51 |
| | Behavior | normal | normal | sleep/move | sleep/move | sleep/move |

TABLE 3B

Parameters in the Determination of the Effect of the Purine Derivatives on Core Body Temperature After 30 Minutes

| Animal # | Parameters | Time | | | | | | |
|---|---|---|---|---|---|---|---|---|
| | | 1 h | 1.5 h | 2 h | 2.5 h | 3 h | 3.5 h | 4 h |
| 1 | Rectal Temperature | 32 | 29 | 27 | 25 | 24 | 23 | 21 |
| | Respiration Rate (/min) | 42 | 45 | 54 | 51 | 42 | 42 | 42 |
| | Behavior | sleep | sleep | sleep | sleep | sleep | sleep | sleep |
| 2 | Rectal Temperaure | 33 | 30 | 28 | 27 | 26 | 25 | 25 |
| | Respiration Rate (/min) | 36 | 36 | 36 | 30 | 27 | 24 | 27 |
| | Behavior | sleep | sleep | sleep | sleep | sleep | sleep | sleep |

After the experiments, the animals were kept in the animal room and their behavior observed. The data set forth in Tables 3A and 3B indicate that Compound I'-1, an illustrative Purine Derivative, reduces an animal's core body temperature.

5.16 Example 16

Determination of the Effect of the Purine Derivatives on Treatment or Prevention of Glaucoma with Intraocular Hypertension The effect of an illustrative Purine Derivative on intraocular pressure (IOP) was examined in New Zealand white rabbits. New Zealand white rabbits undergo a circadian change in intraocular pressure, such that lowest pressure values occur in the early morning and peak pressure values occur in the afternoon. This circadian rhythm is demonstrated in FIGS. 1-5 on the day before the study (i.e., t=−25 hours to t=0 hours). Consistency of measurements is indicated by the fact the intraocular pressure at t=−23 hours and t=25 hours is essentially the same (see FIGS. 1-5).

Compound I'-1 was dissolved in saline, at concentrations 0.3, 1.0, 3.0, 10.0, and 30.0 mg/mL. One rabbit was administered with each each dose level. One drop (about 100 μL) of the saline solution of Compound I'-1 was applied to the external surface of one eye of each rabbit. Compound I'-1 was administered at t=0 hours, 3 hours after the animal house dark period ended (lights came on in the rabbit house at t=−3 hours). Thus, Compound I'-1 was administered when the level of intraocular pressure was low relative to other timepoints during the day and night. After administration with Compound I'-1, the intraocular pressure did not increase to the normal day values (see FIGS. 1-5). For all administered concentrations of Compound I'-1, the lowest intraocular pressure values were in the range of 3 to 4 mmHg, at a timepoint that a New Zeland white rabbit would be expected to have intraocular pressure values of 11 to 13 mmHg. Thus, treatment with Compound I'-1 resulted in a reduction of intraocular pressure values by 8 to 10 mmHg, relative to expected values.

Duration of the effect of Compound I'-1 varied according to the magnitude of the dose. Recovery of intraocular pressure values to normal levels occurred at about t=6 hours, when the administered concentration of Compound I'-1 was 0.3 mg/mL (FIG. 1), and beyond t=7 hours, when the administered concentration of Compound I'-1 was 30 mg/mL (FIG. 5). No eye irritation was observed in any animal.

The data set forth in FIGS. 1-5 indicate that Compound I'-1, an illustrative Purine Derivative, reduces an animal's intraocular pressure and, accordingly, is useful for treating or preventing glaucoma with intraocular hypertension.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

All references cited herein are incorporated by reference in their entirety.

What is claimed is:

1. A compound having the formula

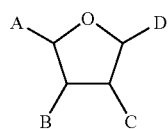

(I)

or a pharmaceutically acceptable salt thereof, wherein
A is —CH$_2$OH;
B and C are OH;
D is

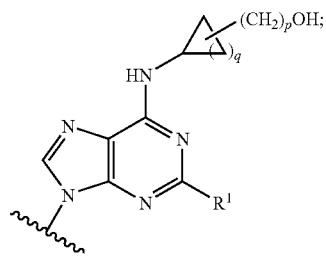

A and B are trans with respect to each other;
B and C are cis with respect to each other;
C and D are cis or trans with respect to each other;
R$^1$ is —H, or -halo;
each p is an integer ranging from 1 to 6; and
each q is an integer ranging from 1 to 6.

2. The compound of claim 1, wherein q is 3.
3. The compound of claim 1, wherein q is 4.
4. The compound of claim 1, wherein p is 1.
5. The compound of claim 2, wherein p is 1.
6. The compound of claim 3, wherein p is 1.
7. The compound of claim 1, wherein R$^1$ is —H.
8. The compound of claim 1, wherein R$^1$ is -halo.
9. The compound of claim 8, wherein R$^1$ is —Cl.
10. The compound of claim 2, wherein p is 1 and R$^1$ is —H.
11. The compound of claim 2, wherein p is land R$^1$ is —Cl.
12. The compound of claim 3, wherein p island R$^1$ is —H.
13. The compound of claim 3, wherein p is 1 and R$^1$ is —Cl.
14. The compound of claim 1 having the structure:

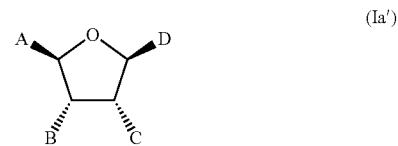

(Ia')

or a pharmaceutically acceptable salt thereof.

15. The compound of claim 14 having the structure:

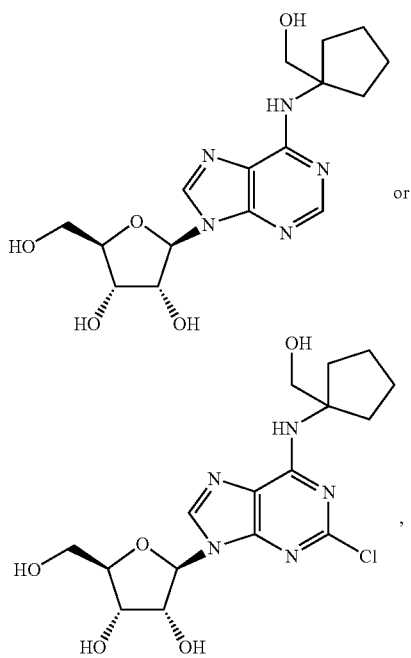

or a pharmaceutically acceptable salt thereof.

16. A therapeutic composition comprising an effective amount of a compound or a pharmaceutically acceptable salt of the compound of claim 1 and a physiologically acceptable carrier or vehicle.

17. A therapeutic composition comprising an effective amount of a compound or a pharmaceutically acceptable salt of the compound of claim 14 and a physiologically acceptable carrier or vehicle.

18. A therapeutic composition comprising an effective amount of a compound or a pharmaceutically acceptable salt of the compound of claim 15 and a physiologically acceptable carrier or vehicle.
19. The compound of claim 1 having the structure:
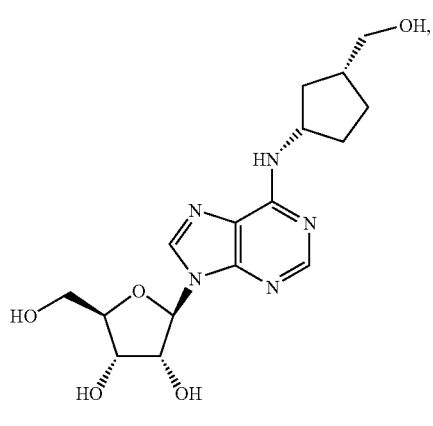
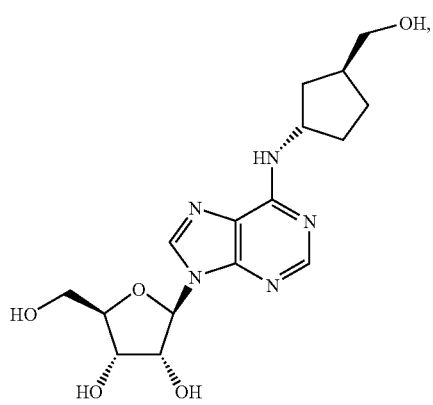
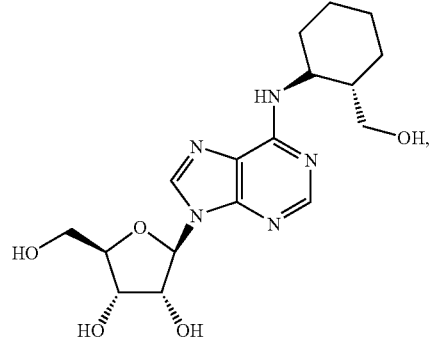
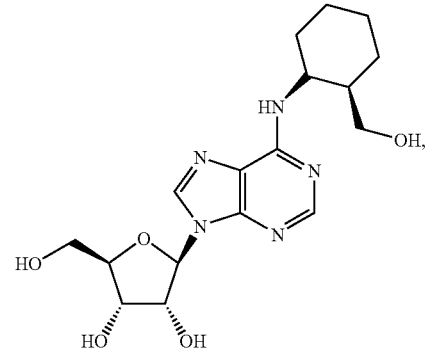
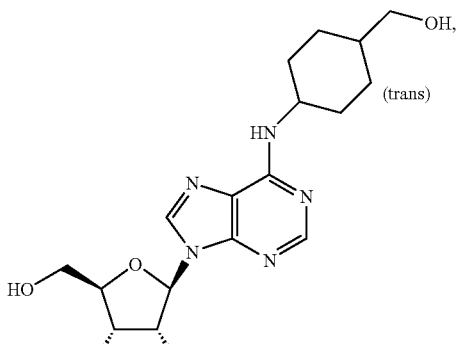
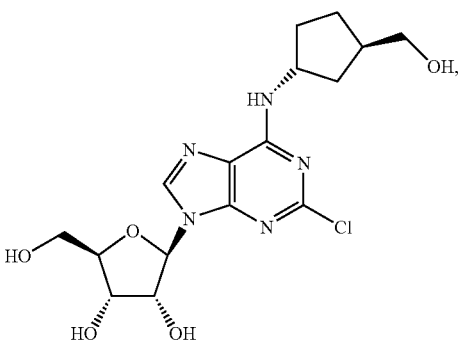
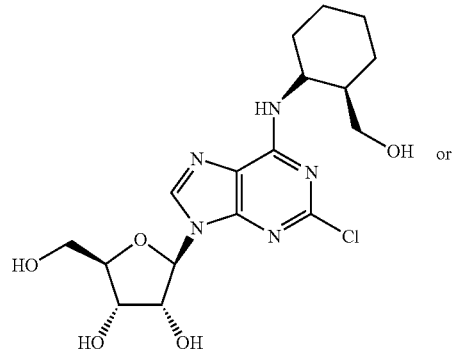
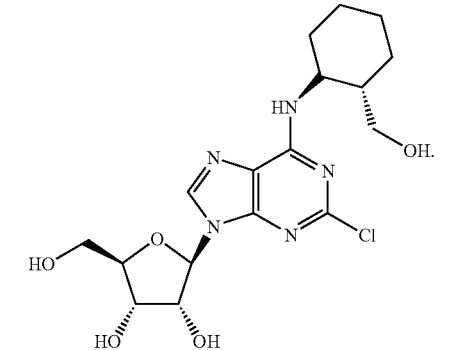
or a pharmaceutically acceptable salt thereof.

20. A compound having the formula:
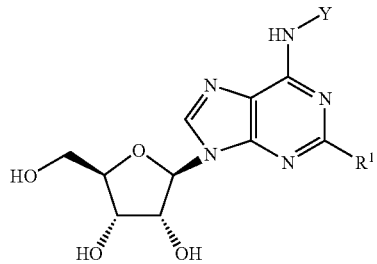
wherein
R¹ is H, Cl, CN, NH₂ or OCH₃; and
Y is
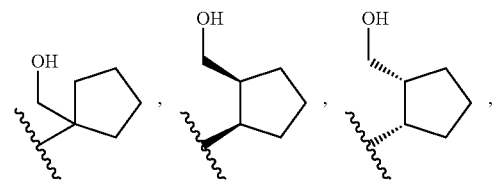
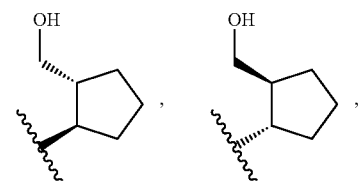
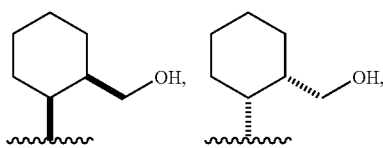
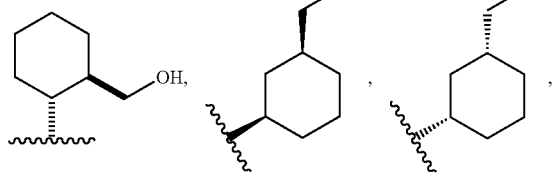
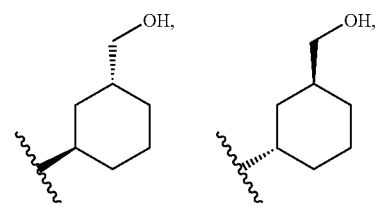
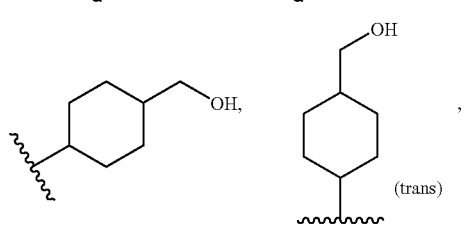
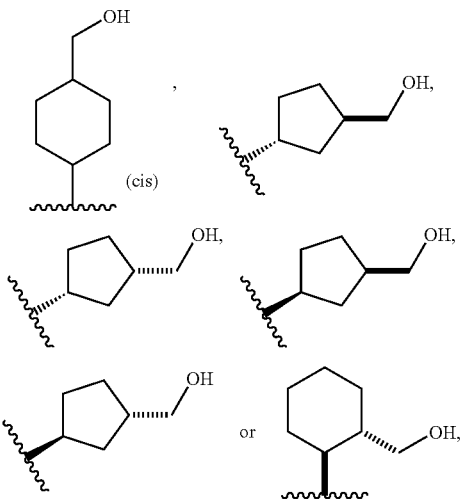
or a pharmaceutically acceptable salt thereof.
21. The compound of claim 20, wherein R¹ is H.
22. The compound of claim 21, wherein Y is
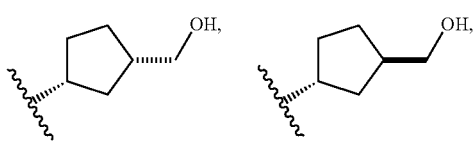
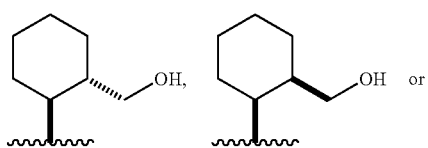
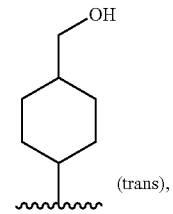
23. The compound of claim 20, wherein R¹ is Cl.
24. The compound of claim 23, wherein Y is
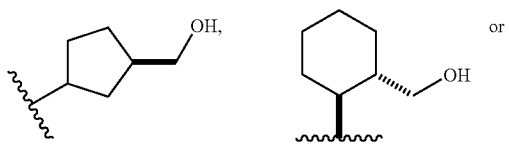
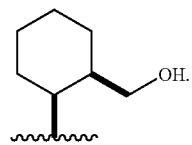

25. A compound having the formula:

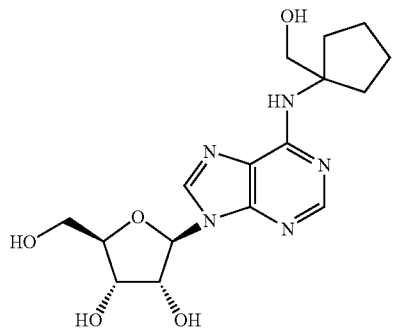

or a pharmaceutically acceptable salt thereof.

26. A compound having the formula:

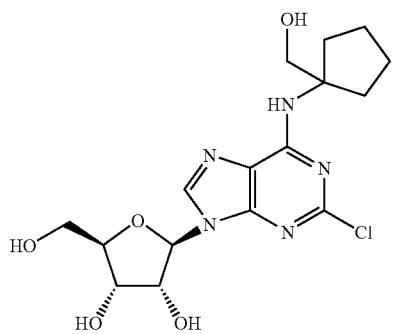

or a pharmaceutically acceptable salt thereof.

27. A method for treating an ophthalmic condition by reducing intraocular pressure, the method comprising administering to an animal in need thereof an effective amount of the compound or a pharmaceutically acceptable salt of the compound of claim 20.

28. A method for reducing an animal's core body temperature, the method comprising administering to an animal in need thereof an effective amount of the compound or a pharmaceutically acceptable salt of the compound of claim 20.

29. The method of any one of claims 27 or 28, wherein said compound is selected from the group consisting of:

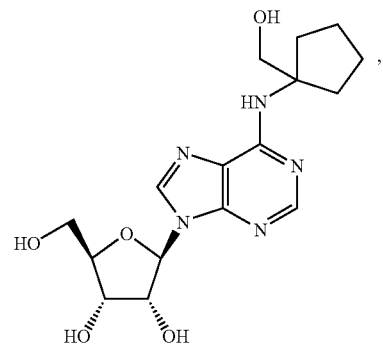

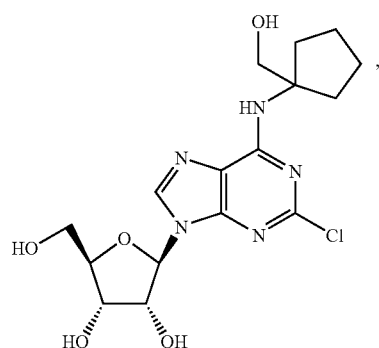

-continued

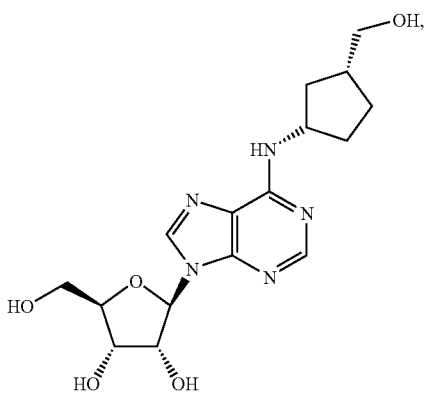

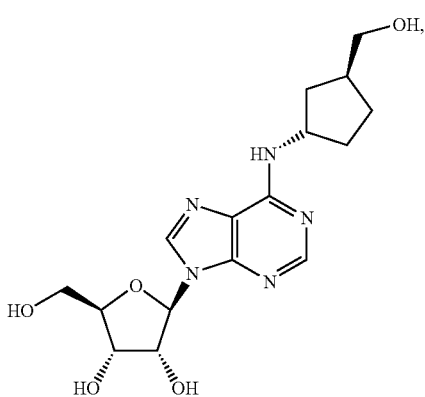

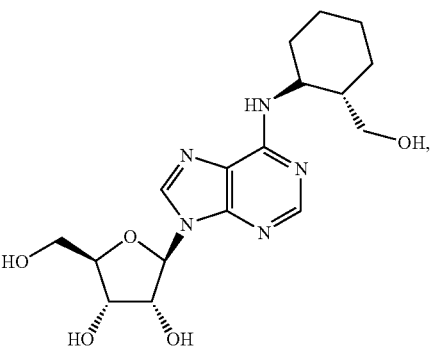

-continued

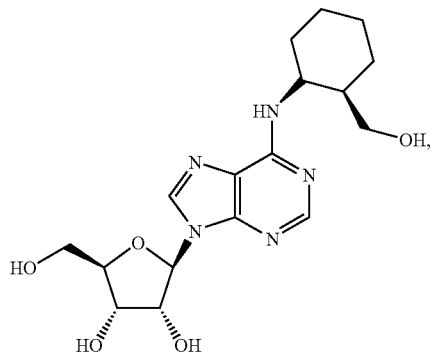

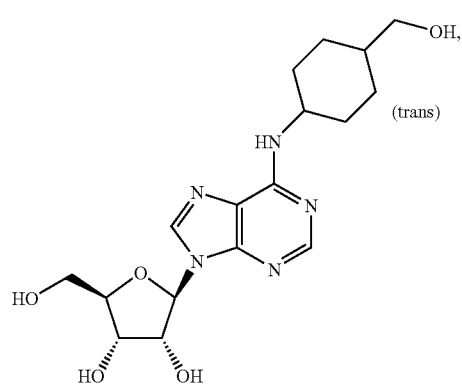

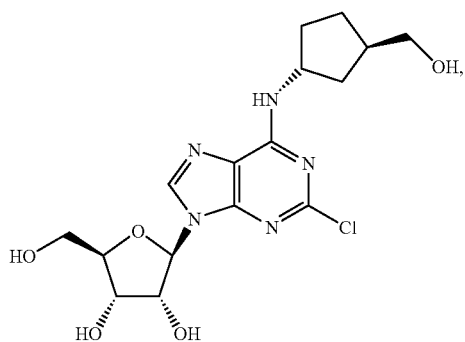

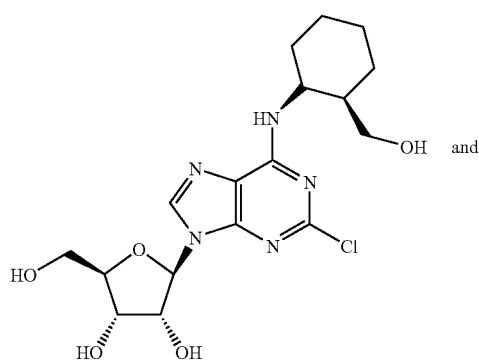

-continued

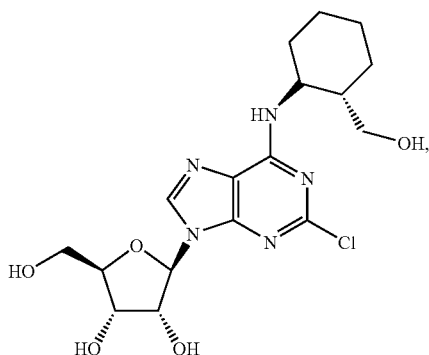

or a pharmaceutically acceptable salt thereof.

30. A method for treating an ophthalmic condition by reducing intraocular pressure, the method comprising administering to an animal in need thereof an effective amount of a compound of the formula:

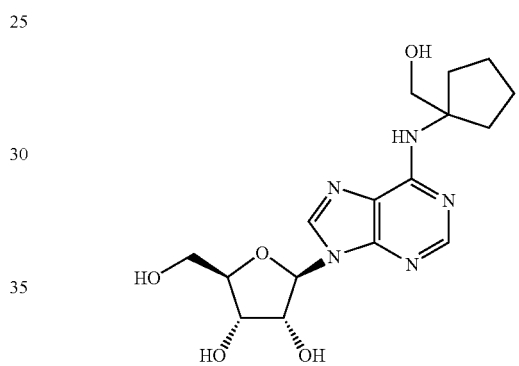

or a pharmaceutically acceptable salt thereof.

31. A method for reducing an animal's core body temperature, the method comprising administering to an animal in need thereof an effective amount of a compound having the formula:

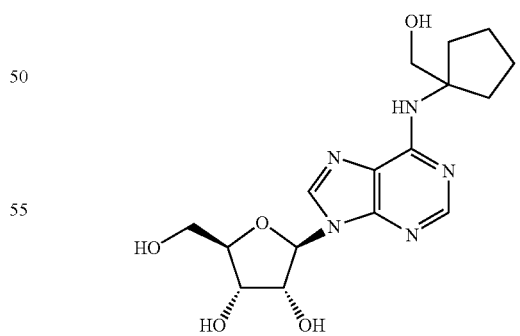

or a pharmaceutically acceptable salt of thereof.

32. A method for reducing an animal's rate of oxygen consumption, the method comprising administering to an animal in need thereof an effective amount a compound having the formula:

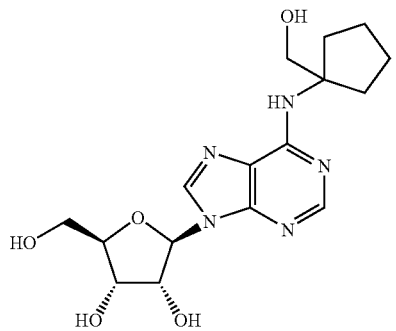

or a pharmaceutically acceptable salt of thereof.

33. A method for treating an ophthalmic condition by reducing intraocular pressure, the method comprising administering to an animal in need thereof an effective amount of a compound of the formula:

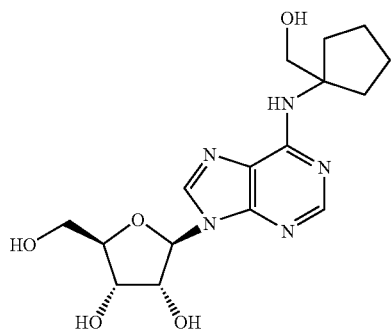

or a pharmaceutically acceptable salt thereof.

34. A method for reducing an animal's core body temperature, the method comprising administering to an animal in need thereof an effective amount of a compound having the formula:

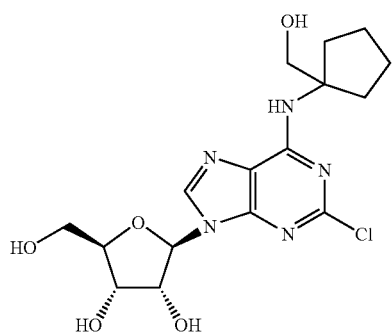

or a pharmaceutically acceptable salt of thereof.

35. A method for reducing an animal's rate of oxygen consumption, the method comprising administering to an animal in need thereof an effective amount a compound having the formula:

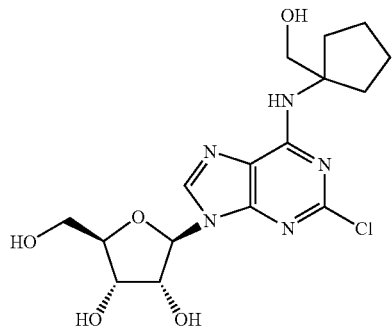

or a pharmaceutically acceptable salt of thereof.

* * * * *